(12) United States Patent
Struik et al.

(10) Patent No.: US 10,898,208 B2
(45) Date of Patent: Jan. 26, 2021

(54) SYSTEM FOR CONNECTING A CONNECTING DEVICE, IN PARTICULAR A DISTRACTOR, TO A BONE

(71) Applicant: ArthroSave Holding B.V., Culemborg (NL)

(72) Inventors: Thijmen Struik, Montfoort (NL); Floris Paulus Jacobus Gerardus Lafeber, Houten (NL); Karianne Hilde Lindenhovius, De Meern (NL); Petrus Maria van Roermund, Amsterdam (NL); Vincent Marianus Cloostermans, Enschede (NL); Simon Carl Mastbergen, Vianen (NL)

(73) Assignee: ArthroSave Holding B.V., Culemborg (NL)

( * ) Notice: Subject to any disclaimer, the term of this patent is extended or adjusted under 35 U.S.C. 154(b) by 196 days.

(21) Appl. No.: 15/748,398

(22) PCT Filed: Jul. 30, 2015

(86) PCT No.: PCT/EP2015/067547
§ 371 (c)(1),
(2) Date: Jan. 29, 2018

(87) PCT Pub. No.: WO2017/016611
PCT Pub. Date: Feb. 2, 2017

(65) Prior Publication Data
US 2018/0221034 A1    Aug. 9, 2018

(51) Int. Cl.
*A61B 17/17* (2006.01)
*A61B 17/64* (2006.01)
(Continued)

(52) U.S. Cl.
CPC ........ *A61B 17/171* (2013.01); *A61B 17/6466* (2013.01); *A61B 17/66* (2013.01); *A61B 2017/90* (2013.01)

(58) Field of Classification Search
CPC . A61B 17/17; A61B 17/6466; A61B 17/6458; A61B 17/6483; A61B 17/64;
(Continued)

(56) References Cited

U.S. PATENT DOCUMENTS 7,637,915 B2 * 12/2009 Parmer ................. A61B 90/11
606/108
9,161,818 B2 * 10/2015 Arthur ............... A61B 17/8816
(Continued)

FOREIGN PATENT DOCUMENTS

JP        2014233571 A      12/2014

*Primary Examiner* — Matthew J Lawson
(74) *Attorney, Agent, or Firm* — Peter W. Schroen; Bret E. Field; Bozicevic, Field & Francis LLP

(57) ABSTRACT

System for connecting a connection device to a bone with a bone pin, wherein the connection device is provided with an opening for receiving the bone pin, wherein the system comprises: —said connection device; —a guiding tube arranged to guide the bone pin from the connection device to the bone for connecting the bone pin to the bone, wherein the inner diameter of the guiding tube corresponds to the outer diameter of the bone pin and wherein the guiding tube can be slidably received in the opening, the guiding tube being slidable with respect to the connection device along an axis parallel to a longitudinal axis of the opening; —a locking device arranged to be received in the opening of the connection device and arranged to engage the bone pin for locking the bone pin with respect to the connection device, wherein the guiding tube is movable with respect to the connection device and bone pin such that the guiding tube is removable from the combination of the bone pin and the
(Continued)

connection device and wherein the locking device is arranged to lock the bone pin after removal of the guiding tube.

26 Claims, 16 Drawing Sheets

(51) Int. Cl.
*A61B 17/66* (2006.01)
*A61B 17/90* (2006.01)

(58) Field of Classification Search
CPC ............ A61B 17/6414; A61B 17/6416; A61B 17/6425
See application file for complete search history.

(56) References Cited

U.S. PATENT DOCUMENTS

| | | | |
|---|---|---|---|
| 2007/0123857 A1 | 5/2007 | Deffenbaugh et al. | |
| 2012/0150186 A1* | 6/2012 | Hajianpour | A61B 17/171 606/59 |
| 2012/0253410 A1* | 10/2012 | Taylor | A61B 17/6458 606/329 |
| 2014/0066931 A1 | 3/2014 | Myers et al. | |

\* cited by examiner

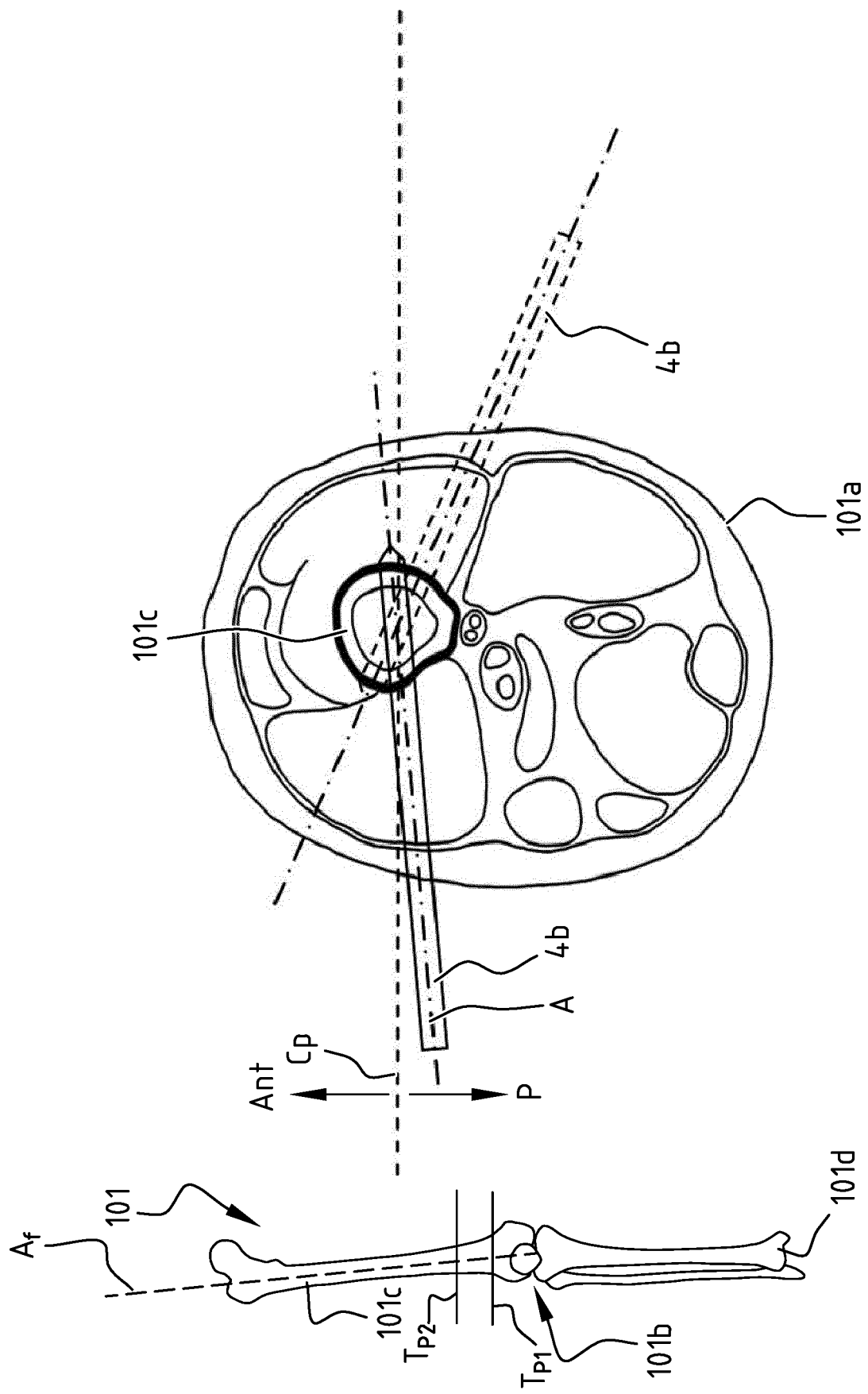

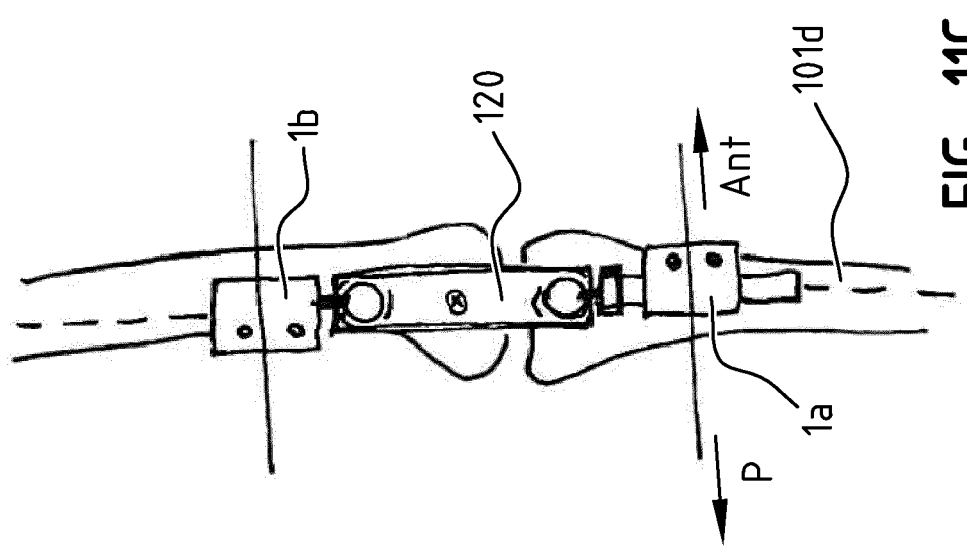
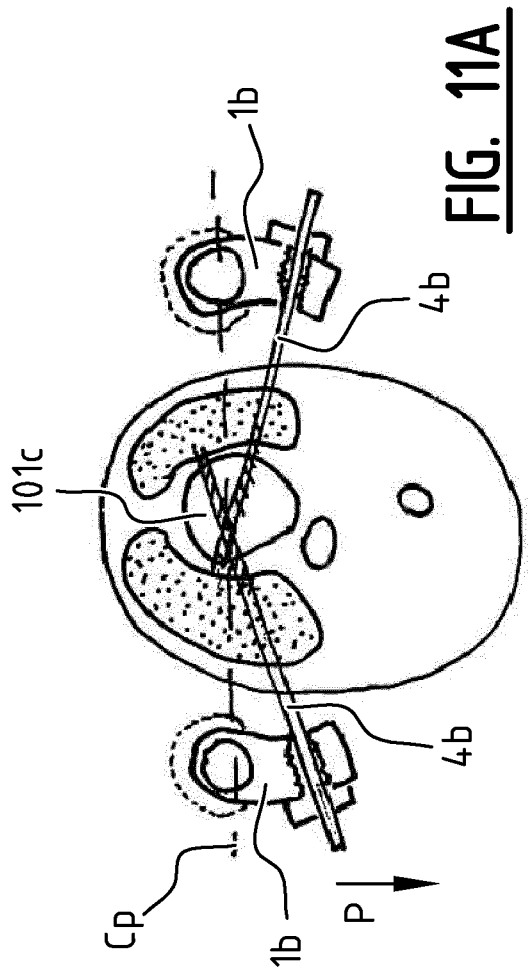
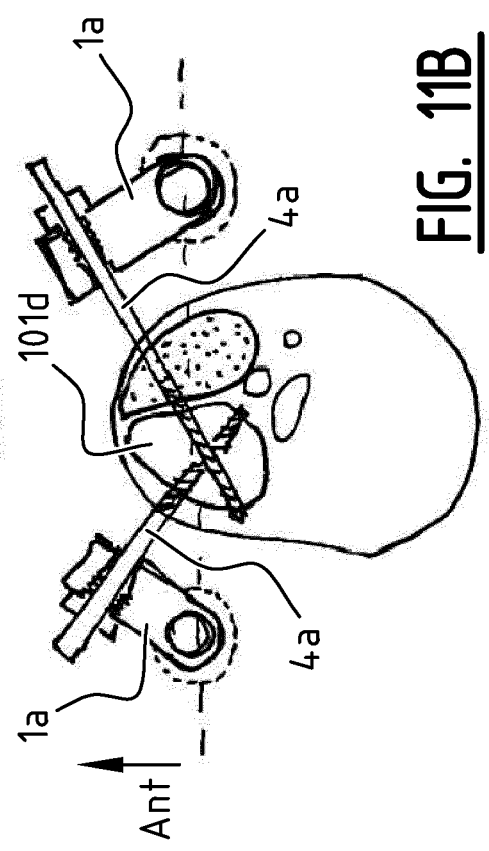
FIG. 11C
FIG. 11A
FIG. 11B

SYSTEM FOR CONNECTING A CONNECTING DEVICE, IN PARTICULAR A DISTRACTOR, TO A BONE

The present invention relates to a system and method for connecting a connection device to a bone with a bone pin. The invention further relates to an external orthopaedic device, in particular a distractor, connecting different bones or bone parts. The invention further relates to a method for connecting an external distractor between at least two bone parts of a patient.

In the field of trauma surgery as well as in orthopaedics, external fixators are commonly used for treatment of complex fractures, stabilization of bony structures or joints, and in bone lengthening procedures. In external fixation, multiple bones or bone fragments are connected with a frame for providing additional structure to the bones, where fixation is achieved with bone pins, which can partially or fully penetrate the bone, providing one or more options per bone pin for attachment of an external device. More complex approaches comprise the use of ring fixators, or Ilizarov frames, which enable fixation of multiple bones with bone pins or tensioned wires, such that bones are reachable from nearly any direction preferably perpendicular to the longitudinal bone axis. For fixation of less bone parts, unilateral fixators, generally connected with multiple sets of two or three bone pins, may provide the required additional structure for a treatment.

Various frame designs provide, besides fixation, additional features like adjustability of the frame for reconfiguration of the fixated bone parts after fixation and without replacing the bone pins, dynamization between the entry sites for stimulation of bone growth, or joint motion in case of fixation of multiple bones forming a joint. Recent development introduced externally fixated devices in treatment strategies for joint diseases like osteoarthritis where affected joints can be bridged by a dedicated external fixator for application of joint distraction.

Osteoarthritis is a degenerative joint disorder, progressive over time, characterized by cartilage damage and loss, changes in peri-articular bone, synovial inflammation, and peri-articular muscle and ligament changes. These tissue changes are considered causative for clinical characteristics like pain, stiffness, and functional disabilities (Bijlsma J W J et al. Lancet 2011; 377: 2115-26). Knee osteoarthritis is the most prevalent form of osteoarthritis with an increasing socioeconomic and healthcare burden. Due to, amongst others, aging of the population and increase in obesity at a young age occurrence of knee osteoarthritis is estimated to increase significantly in the forthcoming years.

Few options are available for treatment of end-stage knee osteoarthritis and none have clearly been shown to halt or reverse tissue structure damage. Conservative treatment focuses on minimizing functional disability and pain relief with anti-inflammatory treatment when indicated (Bijlsma J W J et al. Lancet 2011; 377: 2115-26).

In case of uni-lateral tibio-femoral knee osteoarthritis, high tibial osteotomy or unilateral knee arthroplasty as well as new options like partial medial joint unloading by subcutaneous placed devices may provide a temporary solution. However, these techniques are rather invasive. Most importantly these techniques do not serve bi-lateral tibio-femoral knee osteoarthritis.

Eventually for all these cases a total knee prosthesis is indicated, and joint tissue is removed from the bony ends and replaced by artificial joint components. Unfortunately, these endo-prostheses have a limited life span due to wear and tear of the materials. The younger the patients (the more active they still are) the shorter the life span of a knee prosthesis. In case placed at an age below 65 years the chance for revision surgery is high. These revision surgeries are much more complex and expensive with less good outcome.

Therefore, there is a need for joint preserving treatments, to delay the first total knee prosthesis and with that prevent revision surgery. For specifically such cases, knee joint distraction has been introduced as a bi-lateral tibio-femoral joint preserving procedure. In case of failure of this treatment, the joint is uncompromised and any other treatment, including surgical intervention like hemi prosthesis, osteotomy or a total knee prosthesis remains optional.

Knee joint distraction has quite recently been introduced as a tibio-femoral joint preserving procedure and is more and more accepted as option to postpone placement of a first prosthesis below the age of 65 years. Both clinical improvement and structural tissue regeneration have been demonstrated with clinically relevant duration. (Mastbergen S C et al Nat Rev Rheumatol. 2013; 9: 277-90). This surgical treatment gradually separates the bony ends of a joint to a certain extent, increasing the joint space width with approximately five millimetres, for a limited period of 6-8 weeks.

Separation of the bony ends is achieved with an externally fixated device, connected to the bones forming the joint, with in general half bone pins drilled through soft tissues into both bone cortices. For a stable fixation bone pins are placed at multiple locations in each bone, in case of the knee at the medial and lateral side of femur and tibia. The external device is connected to these bone pins, as such forming a rigid structure enabling fixation of the whole joint and enabling distraction of the joint. Joint loads during application are primarily transduced via the external device and the bone pins, relieving the affected joint. In the distracted configuration, a confined axial displacement remains present when loaded and unloaded, still preventing further wear and tear of the damaged articulating surfaces with the resilience potentially stimulating the regenerating capability of the joint.

As primary functionality, external fixators provide additional stiffness to a bony structure. Stiffness is established by interconnecting bony parts via bone pins to a frame with specifications that suit the chosen treatment strategy. The connection between the external frame, in particular a connection device thereof, and the bone pins should be ensured in order to have advantage of other system features. Due to the variation in optimal position between patients and anatomical sites, establishment of the connection between the bone pins and the frame often requires multiple actions like tightening of multiple bolts from multiple directions, while stability of the connection is not always ensured. Reusability of external devices, and accompanying signs of use like burrs and wear from the cleaning and sterilization procedures, often worsen the reliability of such connections. Since placement of a bone pin requires at least one line of action for attachment to a bone, it is ensured that for every placed bone pin, a certain position and orientation provides sufficient reachability for performing other actions like fixation of the pin to the external frame. A solution which enables use of this ensured line of action provides a more intuitive and easy way of working for the surgeon. Moreover, the established connection can become more reliable when critical components receive inspection previous to every usage, or even are replaced.

A problem associated with known external orthopaedic devices including a system for connecting a connection device to the bone is therefore the heaviness and bulkiness of the existing solutions to frame the bones, because of the use of many components. Moreover, existing solutions require a time consuming surgery process to place the frame optimally to the human body, because of the use of (many) external tools for placement and assembling various system components to a functional structure. A further problem associated with known connection systems is that incorrect or non-optimal placement of bone pins may result in undesirable stress levels in the pin and in the bone structure.

Fixation of the device with half-pins into the bones of the treated joint requires anatomically optimal positioning at each of the bony ends of the joint of interest, such that bone pins do not intersect or interfere with critical tissue structures like nerves and blood vessels, but also not with tendons and muscle bundles and with that reducing the risk for complications or permanent damage. Furthermore, bone pins should not enter the joint capsule. Additionally important bone pins should avoid the area where later in life a prosthesis needs to be placed, so they should be placed at a certain distance from the joint space. Clearly there are for all joints a limited number of preferable anatomical locations where bone pins should be placed for optimal result with minimal damage.

As a result of the preferred anatomically available bone pin locations at each side of the joint and at the different sides of each bone, bone pins might need positional 'misalignment' with respect to mechanics of the external fixation frame, to obtain optimal anatomical positions of the bone pins. In case bone pins are positioned for fixation and distraction of the knee joint, angular misalignment around the mechanical axis of the joint results from the choice for optimal anatomical pin placement.

The interaction of the bone pins with soft tissues is therefore a further problem associated with known external fixation devices such as external distractors. The pin positions and orientation are dictated by the device, such that pins may intersect with fragile soft tissue. Moreover, axial displacement cannot be guaranteed to stay parallel with the longitudinal axis of the tibia, which is preferred. If axial displacement is not parallel to the longitudinal axis of the tibia, the interdistance of the frame and the human leg increases in the length direction of the femur, which is not favourable regarding joint configuration, and which is making this construction uncomfortable for the patient to wear.

It is a goal of the present invention, next to other goals, to provide a system for connecting a connection device to a bone wherein at least one of the above mentioned problems is solved or at least alleviated.

This goal, amongst other goals, is met by a system according to appended claim 1. More specifically, this goal, amongst other goals, is met by a system for connecting a connection device to a bone with a bone pin, wherein the connection device is provided with an opening for receiving the bone pin, wherein the system comprises:
said connection device;
a guiding tube arranged to guide the bone pin from the connection device to the bone for connecting the bone pin to the bone, wherein the inner diameter of the guiding tube corresponds to the outer diameter of the bone pin and wherein the guiding tube can be slidably received in the opening, the guiding tube being slidable with respect to the connection device along an axis parallel to a longitudinal axis of the opening;
a locking device arranged to be received in the opening of the connection device and arranged to engage the bone pin for locking the bone pin with respect to the connection device,
wherein the guiding tube is movable with respect to the connection device and bone pin such that the guiding tube is removable from the combination of the bone pin and the connection device and wherein the locking device is arranged to lock the bone pin after removal of the guiding tube.

The system for connecting a bone pin to a connection device according to the invention allows the connection device, for instance in the form of a connection block of an external orthopaedic device, to be used as a drilling guide such that the trajectory of the bone pin is determined by the configuration of the connection device, in particular the orientation of the opening thereof. After proper guidance of the bone pin using the opening of the connection device, the bone pin can be efficiently locked to the connection device using a locking device which is shaped to be received in the opening of the connecting device and which is arranged to lock the bone pin with respect to the connection device. A simple and efficient connection system that is intuitive to use is herewith provided.

Inserting the bone pins by drilling needs protection of the soft tissues during drilling by a guiding tube, sometimes also referred to as a cannula or sleeve, around the bone pin protecting soft tissue to be harmed by the rotating bone pin during drilling. To enable drilling of a bone pin through the connection device using the guiding tube and subsequent fixation of the bone pin after removal of the guiding tube to the connection device, a locking device is provided. In a preferred embodiment, rotation of the guiding tube is blocked during drilling.

The invention also relates to a method for connecting a connection device to a bone with a system according to invention, wherein the method comprises the steps of:
providing a bone pin in said guiding tube in the opening of the connection device;
guiding the guiding tube to the bone by sliding said guiding tube in the opening of the connection device with respect to said connection device, such that the guiding tube abuts the bone;
inserting the bone pin into the bone;
removing the guiding tube from the combination of the bone pin and the connection device after insertion of the bone pin; and
locking the bone pin with respect to the connection device with said locking device after removal of the guiding tube.

The opening is arranged to slidably receive a guiding tube. This allows adjusting the relative position of the guiding tube to be adjusted with respect to the connection device. It is in particular preferred that the depth of the guiding tube in the patient can be adjusted, such that the guiding tube is adjusted such that the distal end of the guiding tube abuts the bone. This prevents damage to the tissue surrounding the bone upon drilling of the bone pin.

The connection system according to the invention is in particular suitable to connect a bone pin in accordance with a pre-planned trajectory. This trajectory is defined by the orientation of the opening of the connection device. This solves or at least alleviates the problem of incorrect placement of the bone pins, resulting in undesirable stress levels in the pin and in the bone structure, as well as on the device. The guiding tube is therefore preferably slidable in the opening along only the longitudinal axis of the opening. Any other relative movement is preferably prevented. The step of guiding the guiding tube therefore preferably comprises keeping the connection device substantially stationary with respect to the patient.

According to a preferred embodiment, the locking device has an annular body having an outer diameter corresponding to the diameter of the opening of the connection device and an inner diameter suitable for engaging the bone pin. The outer surface having the outer diameter is then arranged to efficiently connect to the connection device due to the matching diameters. As an alternative, or in addition thereto, it may however also be possible that the locking device and the connection device interconnect at another location than the outer surface of the locking device.

The inner surface of the locking device is then arranged to be able to lock the bone pin by engagement. This prevents movement between the locking device and the bone pin, such that also relative moment of the bone pin with respect to the connection device is prevented.

In order to achieve an efficient locking of the bone pin, the locking device according to a preferred embodiment comprises an engaging surface for engaging the bone pin, wherein the engaging surface is movable towards and from said bone pin between an unlocked position, wherein the bone pin is movable with respect to the engaging surface, and a locking position, wherein the engaging surface engages the bone pin for locking said bone pin with respect to the connection device by clamping. The step of locking the bone pin in the method according to the invention therefore preferably comprises engaging the bone pin with an engaging surface of the locking device for clamping said bone pin. The engagement surface is preferably moveable radially inwardly towards the longitudinal axis of the bone pin.

It may be possible that the engagement surface is only movable from the unlocked position to the locked position, such that the bone pin can no longer be loosened after locking with the locking device, preferably with (but not restricted to) plastically deforming either of the components, preferably the locking device. It is however preferred if the engaging surface is also movable from the locked to the unlocked position, such that the bone pins can be loosened if needed.

The engaging surface may for instance be formed on movable or deformable parts of the locking device, such as tongues, which are movable towards and preferably also from the bone pin for locking the bone pin.

Preferably, the locking device has an inner diameter substantially corresponding to the diameter of the bone pin. In this embodiment, the locking device can only be placed in the opening after the removal of the guiding tube, as the guiding tube would not fit in the locking device. Providing a locking device having an inner diameter corresponding to the outer diameter of the bone pin allows a good locking action, as for instance the engagement surface only needs to be displaced over a little distance to obtain a good clamping action.

As an alternative, the locking device has an inner diameter substantially corresponding to the outer diameter of the guiding tube in the unlocked position. This allows the locking device to be already in place in the opening when the guiding tube is guided in the opening. The locking device may then have a guiding function for guiding the guiding tube. When the guiding tube is removed after insertion of the pin in the bone, the engagement surface is moved towards the bone, thereby bridging the wall thickness of the then removed guiding tube, to clamp the bone pin.

In order to be able to efficiently move the engaging surface to the locked position, the opening of the connection device preferably has a tapering diameter, seen along the longitudinal axis of the opening, for moving the engaging surface between the positions, upon longitudinal movement of the locking device with respect to the connection device. The step of locking the bone pin in the method according to the invention then preferably comprises moving the locking device along the longitudinal axis of the opening of the connection device for urging the engaging surface onto the bone pin. The tapering diameter, or at least varying diameter, of the opening then serves as a guiding surface for guiding the engagement surface towards the bone pin for engagement. To further improve the movement of the engaging surface, the locking device preferably comprises a correspondingly shaped tapering outer diameter.

As an alternative, it is also possible that only the locking device has a varying outer diameter, for instance a wedge shape, which urges the engaging surface onto the bone pin upon movement of the locking device into the opening.

According to a further preferred embodiment, the locking device comprises a deformable element arranged to deform in the locked position for engaging the bone pin. The deformable element may for instance be manufactured from a resilient material such as rubber or flexible plastic.

The locking device may be formed as a single unit. This reduces the number of parts. It is however also possible that the locking device comprises an engaging element provided with at least one engaging surface and a separate driving element arranged to move the engaging element along the longitudinal axis of the opening for moving the engaging surface from the unlocked to the locked position. It is for instance possible that the driving element is removed from the opening after locking the bone pin with the engaging element. This prevents accidental loosening of the bone pin.

It is however preferred when the engagement element is arranged to be moved to the locked position upon movement in the opening along the longitudinal axis as explained above, that the engaging element comprises at least one second engaging surface at a distance from the first engaging surface, seen along the longitudinal axis of the opening. This allows clamping at two locations of the bone pin, thereby improving the locking action. The driving element is then preferably provided with an opening for receiving the engaging element and wherein the opening of the driving element has a tapering diameter, seen along the longitudinal axis of the opening, for moving the second engaging surface between the unlocked and locked position upon longitudinal movement of the driving element with respect to the engaging element. Also the engaging element and the driving element are then provided with a cooperating guiding surfaces for urging the engaging surface towards the bone pin. As said, this improves the locking action.

According to a further preferred embodiment, the opening comprises, seen along the longitudinal axis of the opening, a first section having a first diameter and a second section having a second diameter corresponding to the outer diameter of the guiding tube, wherein the first diameter is larger than the second diameter. The change in diameter can be used to move the engaging surface towards the bone pin as mentioned above. The broader section moreover allows receipt of the locking device. To efficiently move the engaging surface as mentioned above, it is further preferred if the opening comprises a tapering section extending between the first and the second sections in which the diameter tapers from the first diameter towards the second diameter. It may be possible that the second section has a limited length, such that the tapering section extends until the end, wherein diameter at the end corresponds to the second diameter.

According to a further preferred embodiment, the opening of the connection device and the locking device are provided with cooperating connecting means for interconnecting the locking device and the connection device. This improves the locking action. Several types of connecting means may be used. It is for instance possible to use a bayonet connection between the locking device and the connection device having a resilient lip engaging in a correspondingly shaped recess or groove. For instance in the case a deformable part is used, it is preferred if the opening is provided with a recess, preferably a groove, for receiving the deformable element for locking the connection device and the locking device.

Efficient locking, while allowing easy manipulation, is however obtained if the locking device and the connection device are provided with cooperating threading.

In case a driving element is used, it is preferred if the driving element and the opening of the connection device are provided with cooperating connecting means. This then locks the driving element with respect to the connection device, while the locking element and the driving element are further preferably also provided with cooperating connecting means.

In order to provide sufficient room for the connecting means, it is preferred if the connecting means are provided in the first, broader section of the opening.

As mentioned above, it is possible that the locking device is arranged to receive and guide the guiding tube. The locking device thereto has a suitable inner diameter. It is however also possible to use a separate guiding element, such that the locking device is dedicated to lock the bone pin. The inner diameter of the locking device may then correspond to the outer diameter of the bone pin as mentioned above. Therefore, a further preferred embodiment of the system further comprises a guiding element for guiding the guiding tube, wherein the guiding element is arranged to be received in the opening of the connection device, wherein the guiding element has an outer diameter corresponding to the diameter of the opening and wherein the guiding element has an inner diameter corresponding to the outer diameter of the guiding tube, wherein the guiding element and the guiding tube are removable from the combination of the bone pin and the connection device. The method according to the invention then preferably further comprises the step of inserting a guiding element in the opening of the connection device and arranging the guiding tube in said guiding element.

After proper guidance of the guiding tube, which in turns guides the bone pin to the bone, the guiding tube and the guiding element are removed. Preferably, the guiding element is removed prior to locking the bone pin. Also the guiding element preferably has an annular body. The outer diameter thereof preferably corresponds to the diameter of the opening, more preferably the annular body has an outer diameter corresponding to the diameter of the first section of the opening. The guiding element is then placed in the first section of the opening and serves to bridge the distance between the inner wall of the opening and the guiding tube.

In order to at least temporary fix the guiding element to the connection device to allow a stable guidance of the guiding tube, the guiding element is preferably provided with corresponding connecting means for interconnecting the guiding element and the connection device. The same connecting means as used for connecting the locking device in the opening are preferably used.

According to a further preferred embodiment wherein a separate driving element is used, said driving element is formed as the guiding element. This reduces the number of parts.

The system according to the invention is in particular useful for connecting a connection device to a bone with two parallel bone pins. A further preferred embodiment of the system according to invention therefore further comprises a second locking device, wherein the connection device comprises a second opening for receiving a second bone pin, wherein the longitudinal axes of the first and the second openings are substantially parallel and wherein the second locking device is arranged to lock the second bone pin after removal of a guiding tube from the second opening. The openings hereby define at least one of the trajectories of the bone pins to be inserted into the bone.

The invention thus further relates to a method for connecting a connection device to the bone with two parallel bone pins, comprising the step of connecting a connection device to the bone with a first bone pin and connecting the connection device to the bone with a second bone pin according to the method according to the invention. Using two parallel bone pins allows adjustment of distance of the connection device with respect to the patient, in particular when the locking device also allows loosening of the bone pins after locking said bone pin.

At least the second bone pin is connected in the above described manner, wherein the opening is used as drilling guide. After placement of a first bone pin at the most appropriate preferred anatomical position, the locations of additional bone pins is (to a certain extend) determined as they are all to be connected to the same external device. To facilitate guiding of the subsequent bone pins for fixation to an external device to the optimal anatomical bone pin positioning there is an advantage to use the for each application specifically designed connection device as bone pin positioning guide or drilling guide. In this way the optimal anatomical position of the bone pin is directly related to an optimal connection to the device and with that the mechanical positioning of the device. Moreover, the optimal anatomical positions can be found intuitively by the guidance of the connecting device.

The first pin may also be fixed using the system and method according to invention. It is however also possible that the step of connecting a connection device to the bone with a first bone pin comprises:
  inserting the bone pin into the bone using a guiding tube;
  removing said guiding tube from the inserted bone pin;
  arranging the connection device onto said inserted bone pin;
  locking the bone pin with respect to the connection device with a locking device,
wherein the method further comprises subsequently connecting the second bone pin according to the method according to the invention. As the position of the connection device with respect to the patient is then fixed, it is an advantage that the slidable guiding tube is adjustable in depth to allow efficient protection of the surrounding tissue upon insertion of the second bone pin.

The invention further relates to an external orthopaedic device arranged to be connected between a first bone part and a second bone part, wherein the orthopaedic device comprises a first connection device according to the invention and a second connection device, preferably also according to the invention. This orthopaedic device can be connected efficiently to the patient as discussed above.

For each application this connecting device will be specifically shaped to guide the bone pins of the second connecting device intuitively to the preferred anatomical bone pin position and to provide optimal positioning of the second connecting device regarding mechanical characteristics of the entire configuration.

The invention further relates to an external orthopaedic device in the form of an external distractor arranged to gradually enlarge the distance between a first bone part and a second bone part, wherein the distractor comprises a first connection device, preferably as defined above, and a second connection device, preferably also as defined above, wherein the first connection device is arranged to be connected to the first bone part with at least one first bone pin and wherein the second connection device is arranged to be connected to the second bone part with at least one second bone pin, wherein the first and second connection devices are interconnected via at least a distraction device, the distraction device having an adjustable length for adjusting the distance between the first and the second connection devices along an adjustment axis.

The distractor device preferable comprises a first part and a second part which are movable with respect to each other along the adjustment axis. The parts may for instance be provided with cooperating threading to allow the adjustment of the length. The distractor device is preferably arranged to adjust the distance between the bone pins while maintaining the structural integrity of the distractor. The distance can thus be adjusted while transferring loads between the first and second bone parts.

The invention therefore also relates to a method for connecting an external distractor between at least two bone parts of a patient, comprising the steps of:
providing an external distractor according to the invention;
connecting the first connection device to the first bone part with at least one bone pin; and
connecting the second connection device to the second bone part with at least one bone pin.

In particular when using the connection system according to the invention, the distractor can efficiently be connected to the patient. It is however noted that the invention is not necessarily limited to a distractor having connection devices according to invention. Addition of other connection devices, such as connection blocks which are known as such, may also be used.

In order to prevent further wear and tear of the damaged articulating surfaces and to potentially stimulate the regenerating capability of the joint, it is preferred if the distractor, in particular the distractor device thereof, comprises resilient means which are arranged for allowing resilient movement along the adjustment axis between the connection devices. The resilient means, for instance in the form of a spring or similar device, then allows small displacements along the adjustment axis.

Although it is possible that the distractor device directly couples the two connection devices, it is preferred if the external distractor further comprises an interconnecting system extending between the first and second connection devices, wherein the interconnecting system is movable between an unlocked position, wherein the connection devices are movable with respect to each other, and a locked position, wherein the mutual positions of the connection devices are fixed. The interconnecting system allows the connection devices to be moved with respect to each other which is in particular useful when connecting the distractor to the patient.

The interconnecting system may for instance comprises at least one lockable hinge, preferably two at either side connected to the connection devices. It is preferred that the interconnecting system is connected to the first and second connection devices with two respective lockable ball joints. This allows the connection devices to be efficiently moved with respect to each other.

A preferred method according the invention therefore preferably further comprises the steps of:
providing the interconnecting system in the unlocked position;
aligning at least one of the connection devices along a predetermined axis with respect to a bone part; and
moving the interconnecting system to the locked position for fixing the mutual positions of the connection devices after alignment.

Preferably, the interconnecting system is moved to the locked position after fixation of the bone pins.

According to a further preferred embodiment, the distraction device is arranged in one of the connection devices, preferably integrally, wherein the interconnecting system extends between the distraction device and the other connection device. More preferably, the ball joint is formed as a part of the distractor device. The distraction device is hereby coupled between a connection device, and the interconnecting device. Although the distraction device may be formed integrally, it is also possible that the distraction device is insofar arranged in one of the connection devices that the minimal distance between the opening in the connection device and the adjustment axis of the distraction device is movable and can be fixed. The location of the opening in the connection device may for instance be adjustable along the adjustment axis of the distraction device to allow adjusting the length of the distractor upon connecting the distractor to the patient.

To allow efficient distraction, in particular of a joint, it is important that the distraction device is correctly aligned with the bone parts. It is in particular preferred if the adjustment axis is aligned with at least one of the longitudinal axes of the bone parts. The step of aligning therefore preferably comprises aligning the longitudinal axis of a bone to be substantially parallel to the adjustment axis of the distraction device. This alignment is more easy to perform if the distraction device is part of one of the connection devices as mentioned above, although this is not strictly necessary.

In order to allow connection of the connection device to a bone without damaging fragile soft tissue (at the anatomically preferred locations), while still allowing axial displacement parallel with the longitudinal axis of the bone (for optimal mechanical performance of the configuration), for instance the tibia, according to a further preferred embodiment the connection device is arranged to receive the bone pin at a certain distance from the adjustment axis.

In order to transduce loads over the joint via the distraction device, correction in alignment is required to ensure optimal unloading of the joint. A certain off-set of the bone pin connection to the axis of the device as well as preferably a certain curvature in the device as will be explained below to obtain optimal anatomical bone pin locations relative to optimal mechanical positioning of the external device will be needed.

According to a further preferred embodiment, at least one of the connection devices is arranged to be connected to the bone part with two substantially parallel bone pins. This improves the stability of the system, while the distance of the connection device and the patient is still adjustable as explained above.

At least one of the steps of connecting a connection device to the respective bone part according to the invention then comprises connecting the connection device to two substantially parallel bone pins. Preferably both connection devices are connected to the bone with two parallel bone pins.

The connection devices thereto preferably comprise two openings for receiving two bone pins. The step of aligning then preferably comprises aligning the connection device such that the openings in the connection device are arranged along an axis substantially parallel to the longitudinal axis of the respective bone part. This allows efficient alignment, wherein the openings in the connection devices are used as a reference for alignment.

It is then preferred if a connection device is provided with two openings for receiving the two bone pins, wherein the openings in the connection device are arranged along an axis at a distance from the pivot point of the ball joint. This creates an offset between the pivot point of the ball joint and the openings through which the bone pins are to extend. This offset allows an improved connection to the bone, at the preferred anatomical positions of the bone pins, preventing potential damage to sensible surrounding tissues. This offset may be specific for specific devices for specific joint bones.

For the connection device provided with the distraction device, it is preferred that when the connection device is provided with two openings for receiving the two bone pins, the openings in the connection device are arranged along an axis substantially parallel to the adjustment axis and such that the two bone pins extend substantially perpendicularly to the adjustment axis. The openings of the connection device can then be used to correctly align the adjustment axis with a predetermined axis of the bone, preferably the longitudinal axis of the bone. It is again preferred if an offset is created between the adjustment axis and an axis onto which the openings in the connection device extend. The openings in the connection device are therefore preferably arranged along an axis at a distance from the adjustment axis.

In particular for distracting a knee joint, it is preferred if one connection device is arranged to receive its bone pins at a distance in a first direction from the adjustment axis or the pivot point, wherein the second connection device is arranged to receive its bone pins at a distance in a second direction from the adjustment axis or the pivot point, the second direction being substantially opposite to the first direction. This protects sensible tissue when inserting the bone pins in accordance with the openings provided at an offset as explained above. Moreover, it provides intuitive positioning of the bone pins at the preferred anatomical locations, guided by the openings in the connection device.

In order to further adapt to the curvature of the patient, it is preferred if the connection device comprises a patient facing surface and an outer surface, wherein an opening extends between the patient facing surface and the outer surface, wherein at least the patient facing surface of the connection device has a curved cross-section, seen in a plane perpendicular to the axis trough the openings. The patient facing surface is then preferably curved in accordance with the curvature of the patient. This provides further intuitive positioning of the bone pins at the preferred anatomical locations, guided by the openings in the connection device.

The distractor is particularly suitable to be used to distract the knee joint. The invention thus also relates to a method for connecting an external distractor between the tibia and the femur, wherein one of the connection devices is connected to the tibia and the other connection device is connected to the femur.

When setting joint distraction to the distraction device, only an increasing joint space width is aimed for, while further joint configuration remains intact. To do so, the distraction direction needs to be orthogonal to both joint surfaces. In case of the knee this means perpendicular to the tibial surface and in the axial direction of the tibia. Specifically to the knee joint, the femoral joint side has a convex, spherical like, surface, while the tibial joint side has a more flattened concave corresponding surface. A direction of distraction orthogonal to both joint sides can be achieved, independent from flexion angle of the joint, by choosing the direction orthogonal to the least spherical surface, or orthogonal to the most flattened surface.

As the connection of the bone pins in the femur is more critical in terms of surrounding tissue which may be damaged, it is preferred if the femur is connected to its connection device prior to connecting the tibia to its connection device.

It is hereby possible that the first pin is inserted into the femur using a guiding tube, to subsequently connect the connection device according to the invention. A second bone pin can then be inserted into the bone using the connection device as drill guide after proper alignment of the connection device, in particular along the longitudinal axis of the bone.

According to a further preferred embodiment, the step of aligning comprises aligning the adjustment axis of the distraction device in the connection device to be substantially parallel to the longitudinal axis of the tibia in the coronal plane and preferably the sagittal plane substantially perpendicular to the tibial plateau. This provides an efficient distraction of the knee joint.

It is hereby noted that it is in particular important that the longitudinal axis of the tibia is aligned with the adjustment axis. It may for instance be possible that the patient is not capable of completely extending the knee, such that the alignment axis is not properly aligned with the longitudinal axis of the femur, such that the connection device on the femur is not aligned with the longitudinal axis of the tibia. The interconnection system then still allows proper alignment of the connection device on the tibia, such that the adjustment axis is parallel to the longitudinal axis of the tibia as explained above.

It is noted that the term aligned as used herein is to be understood that the axes to be aligned are substantially parallel, that is within ±10 degrees with respect to each other.

It is hereby preferred if each of the connection devices is provided with two openings for receiving the two bone pins, wherein the connection devices are aligned such that the openings in the connection device are arranged along axes substantially parallel to the longitudinal axes of the respective bones and such that the two bone pins extend substantially perpendicularly to the longitudinal axes of the respective bones. In order to prevent damage to tissue as already mentioned above, it is then preferred if the step of aligning the connection devices further comprises aligning the adjustment axis and/or the pivot points of the ball joints substantially on the coronal plane, and:
  orienting the openings of the connection devices to be connected to the femur in a posterior position; and/or
  orienting the openings of the connection devices to be connected to the tibia in anterior position.

The distractor as explained may be used as an unilateral distractor. It is however preferred to use the system as a bilateral system for application of knee joint distraction. The invention thus also relates to a method for connecting an external distractor system between at least two bone parts of a patient, comprising the steps of connecting a first external distractor according to the invention at a first side of the bone parts and connecting a second external distractor according to invention at a second side, opposite the first side of the bone parts. It is hereby preferred if the first and second external distractors are arranged substantially on the similar coronal plane on either side of the knee.

The present invention is further illustrated by the following Figures, which show a preferred embodiment of the device and method according to the invention, and are not intended to limit the scope of the invention in any way, wherein:

FIGS. 1a-d schematically show a system and method for connecting a connection device to a bone;

FIGS. 2a-d schematically show a variant of the system of FIG. 1;

FIGS. 3a and b schematically show a variant of fixing a bone pin to a connection device;

Figure 5:
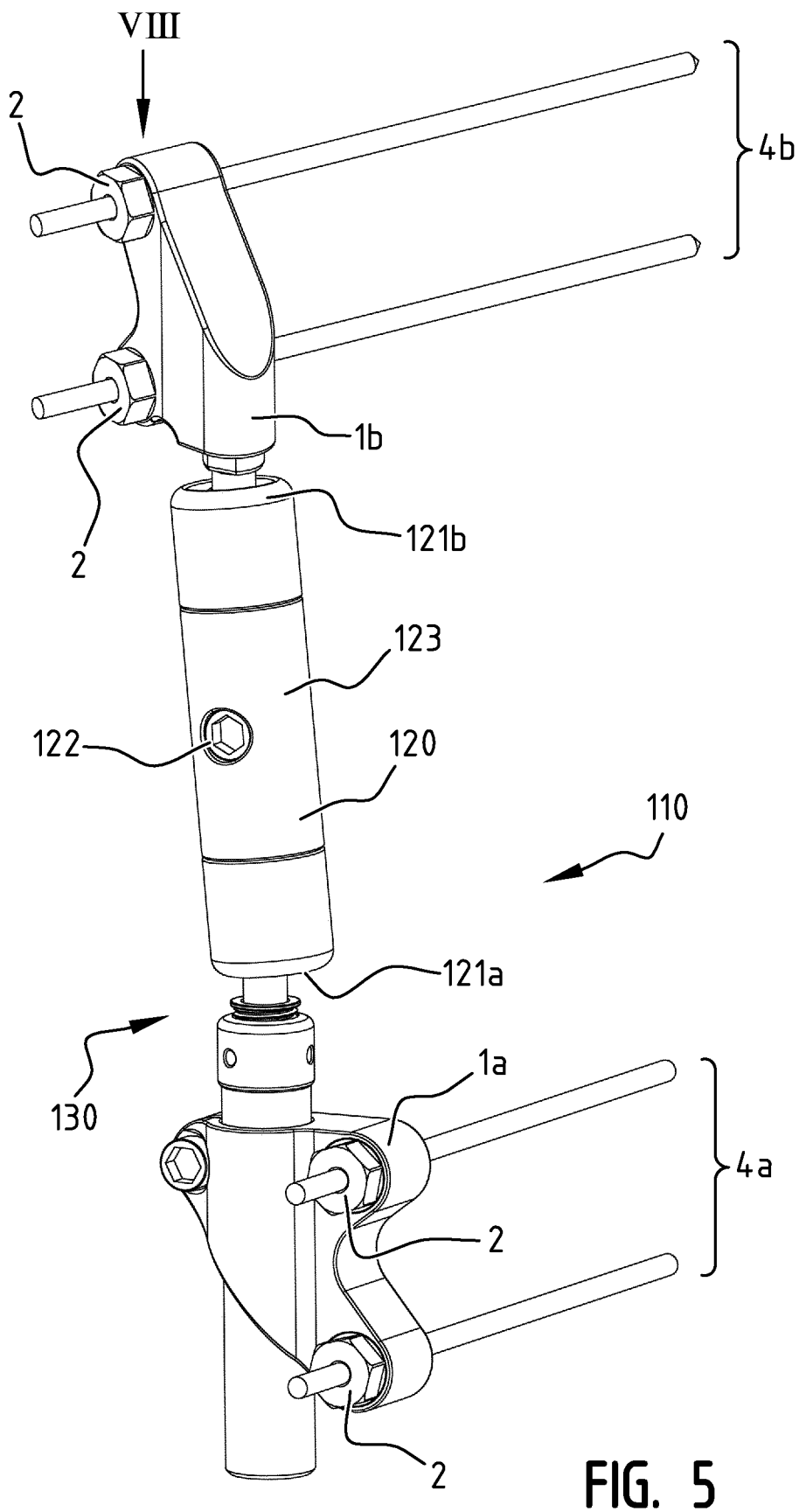
FIG. 5 shows a distractor according to the invention.
Figure 6A:
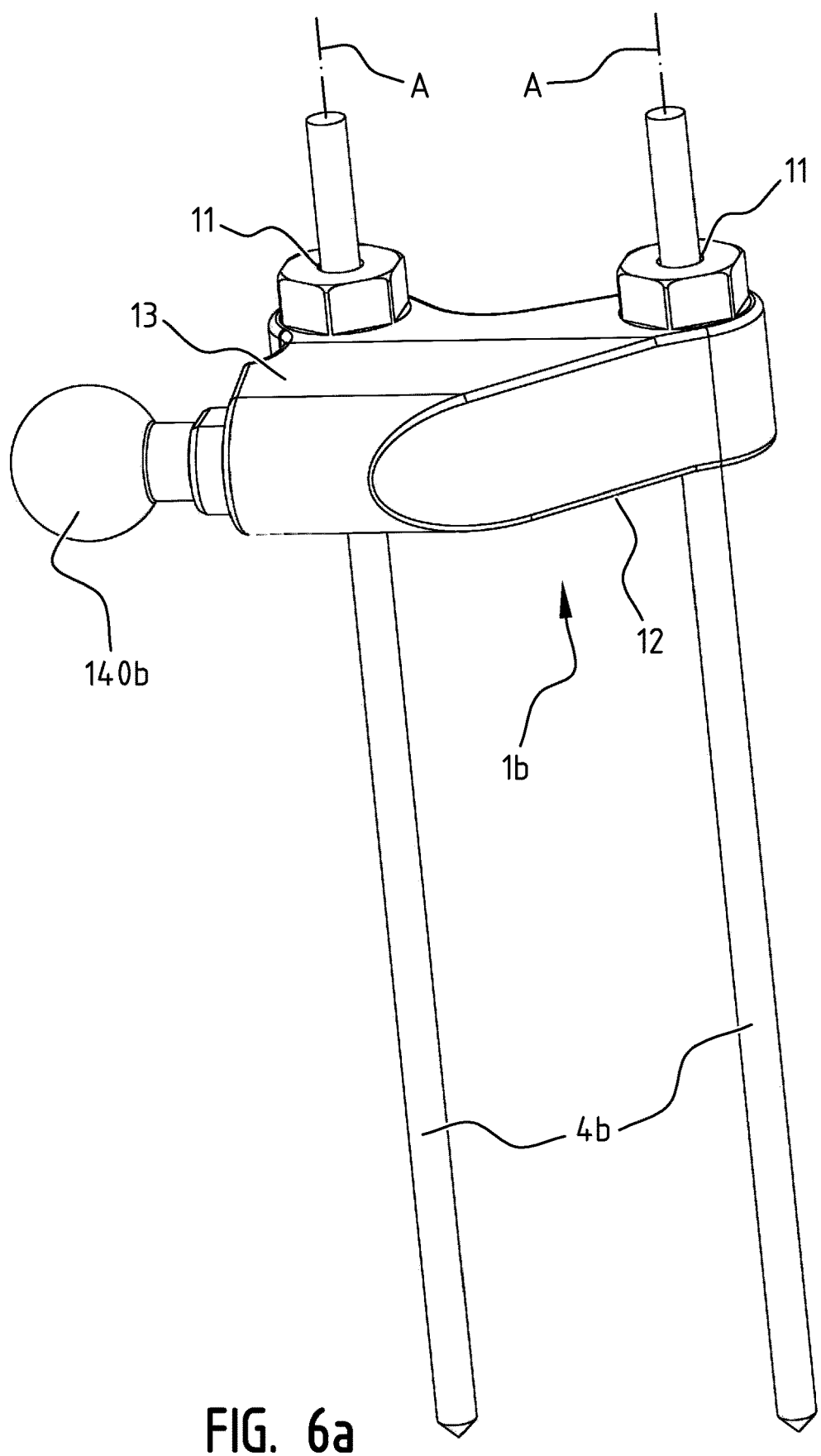
Figure 6B:
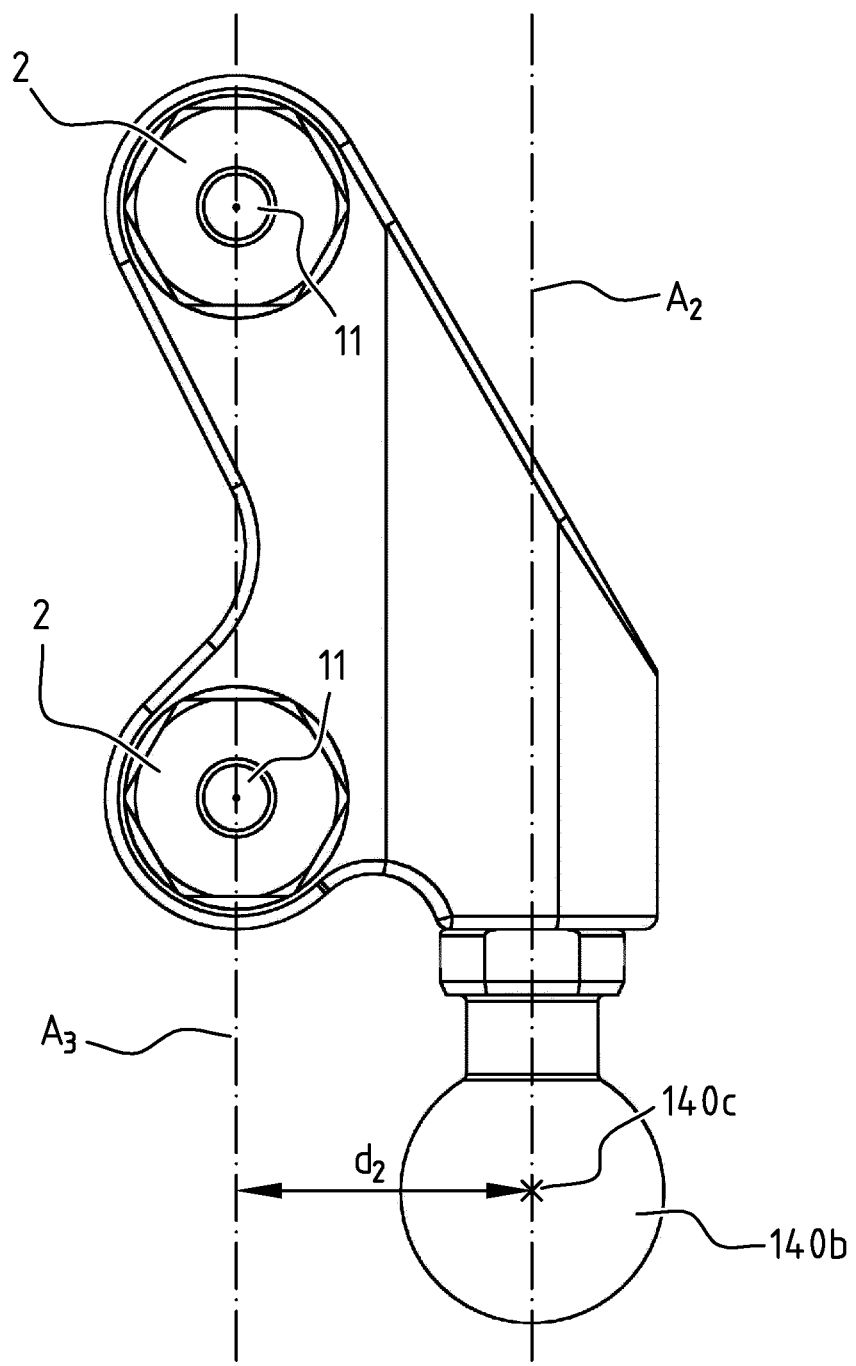
Figure 6C:
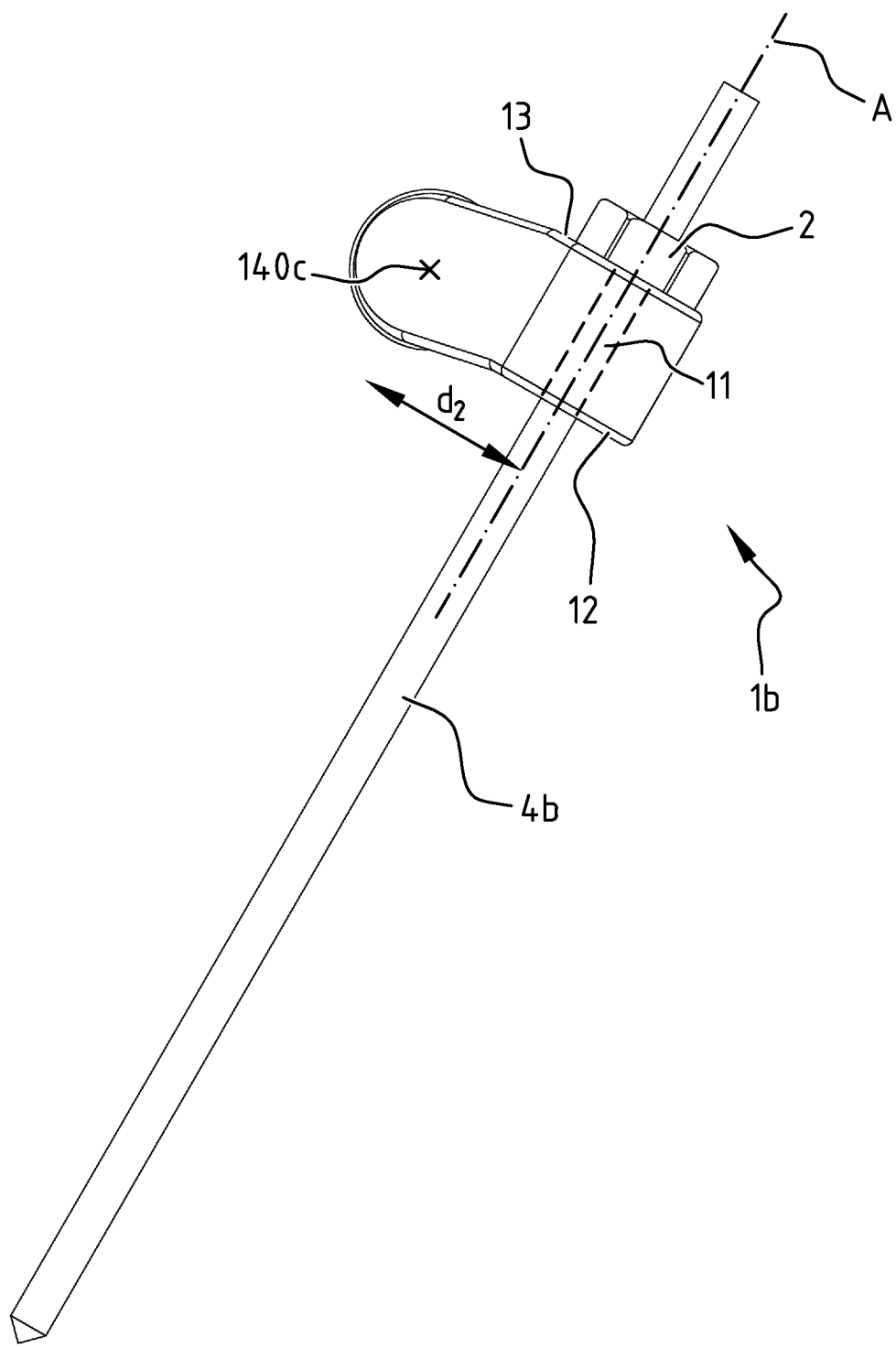
Figure 7A:
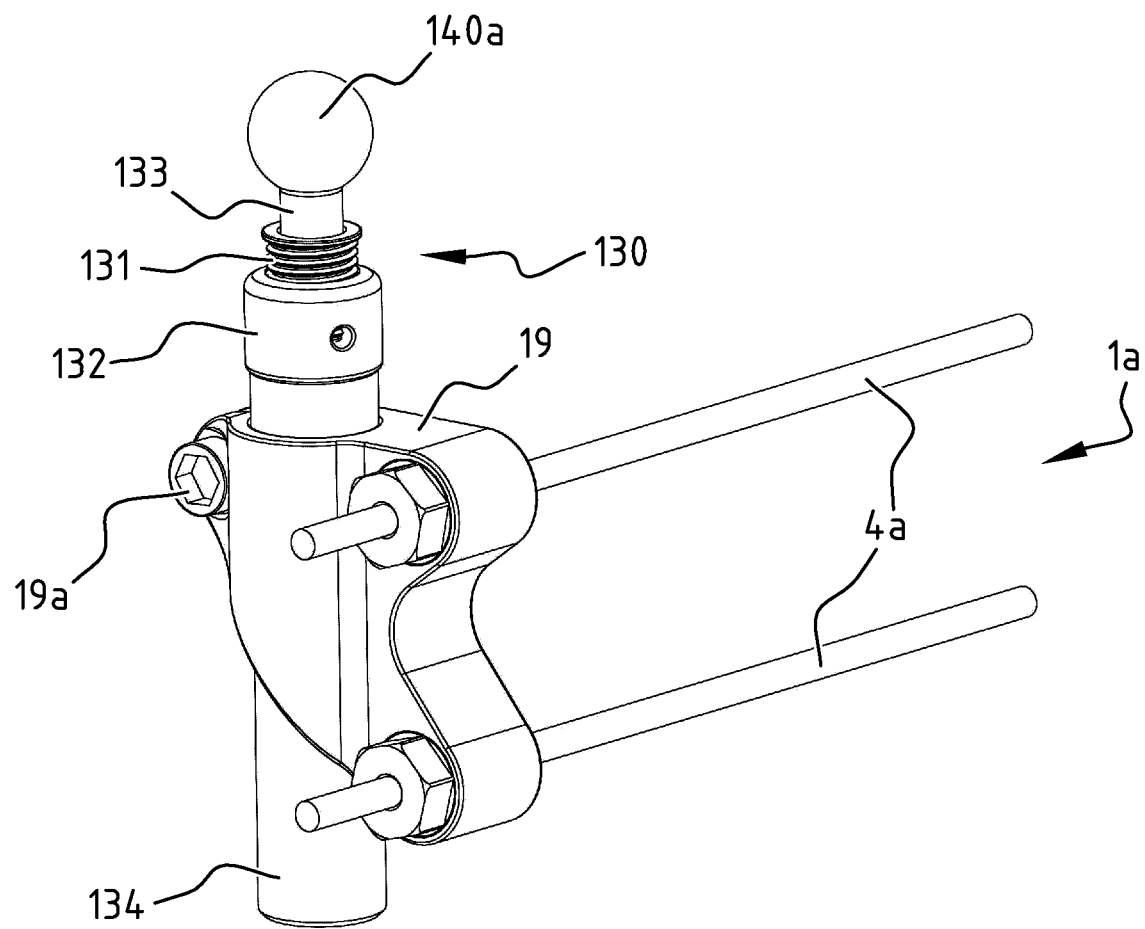
Figure 7B:
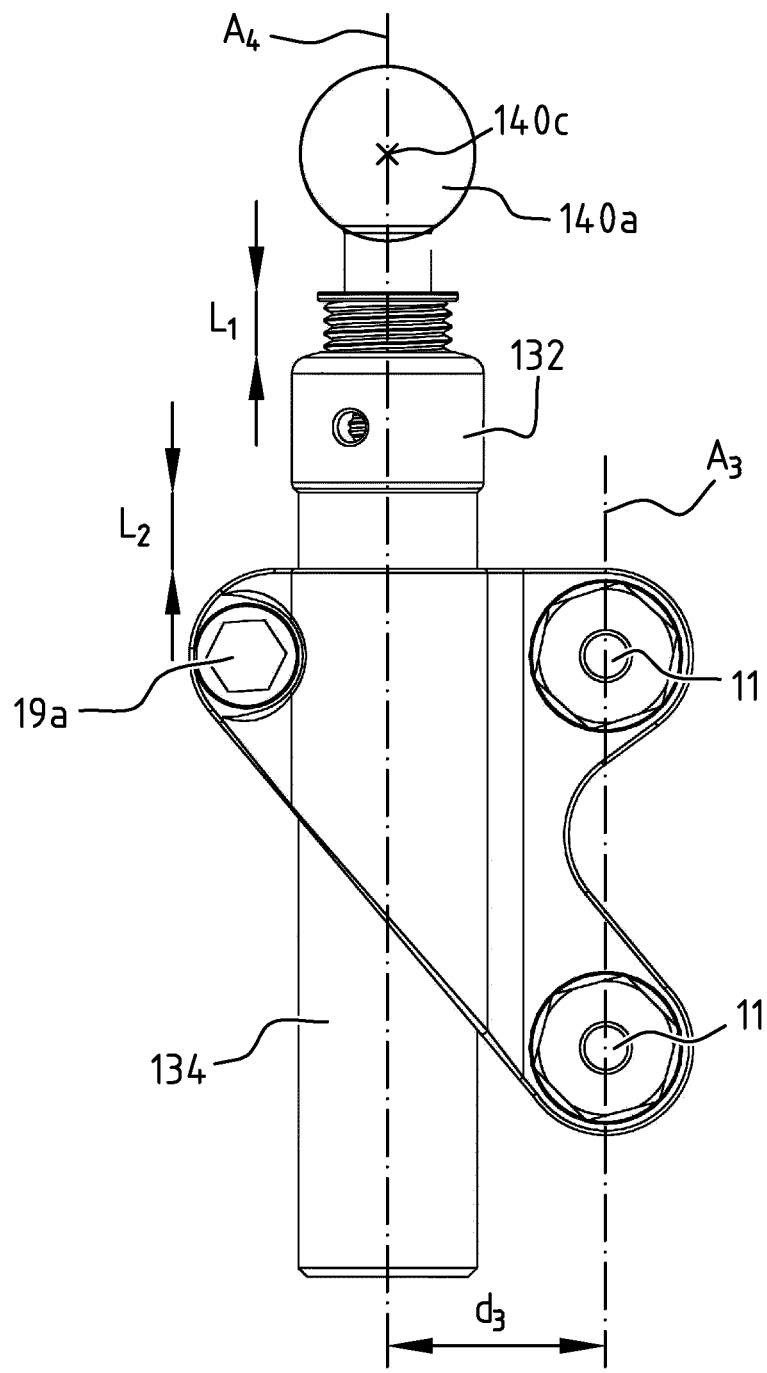
Figure 7C:
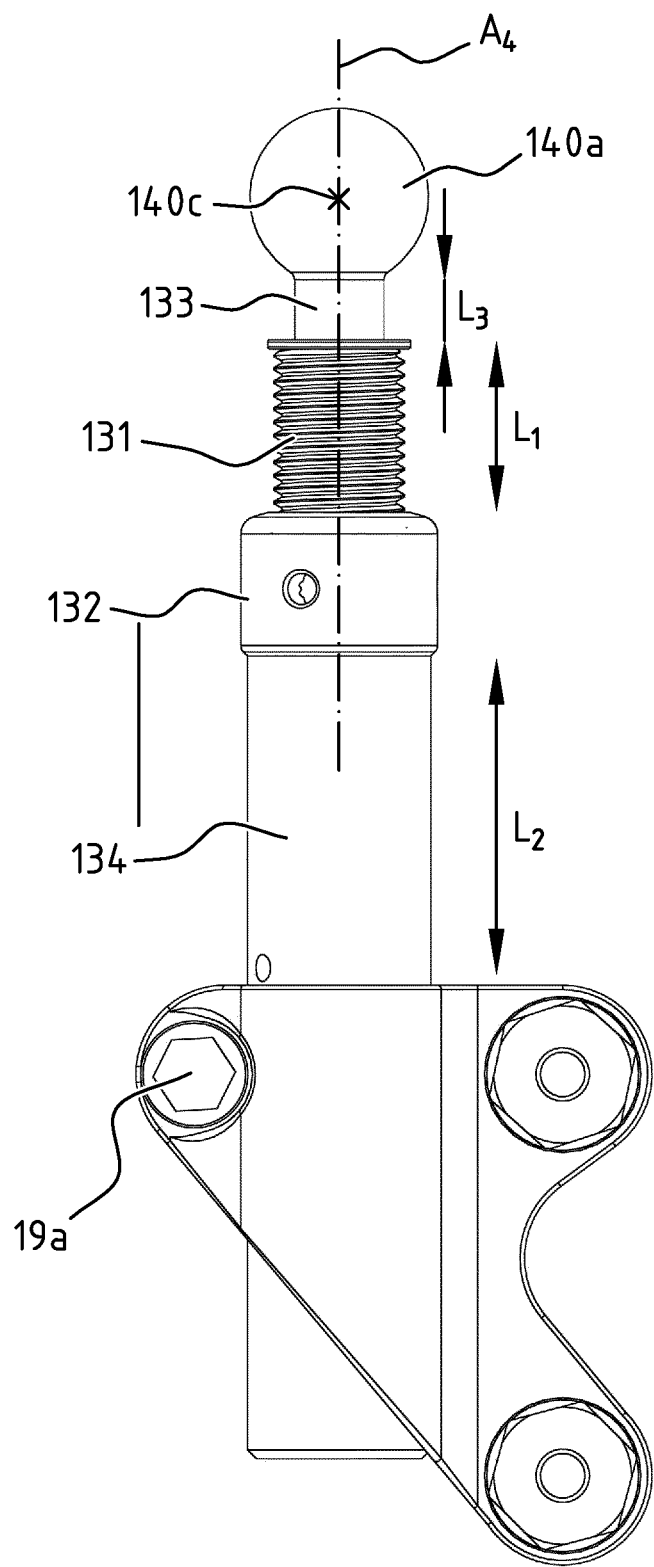
Figure 7D:
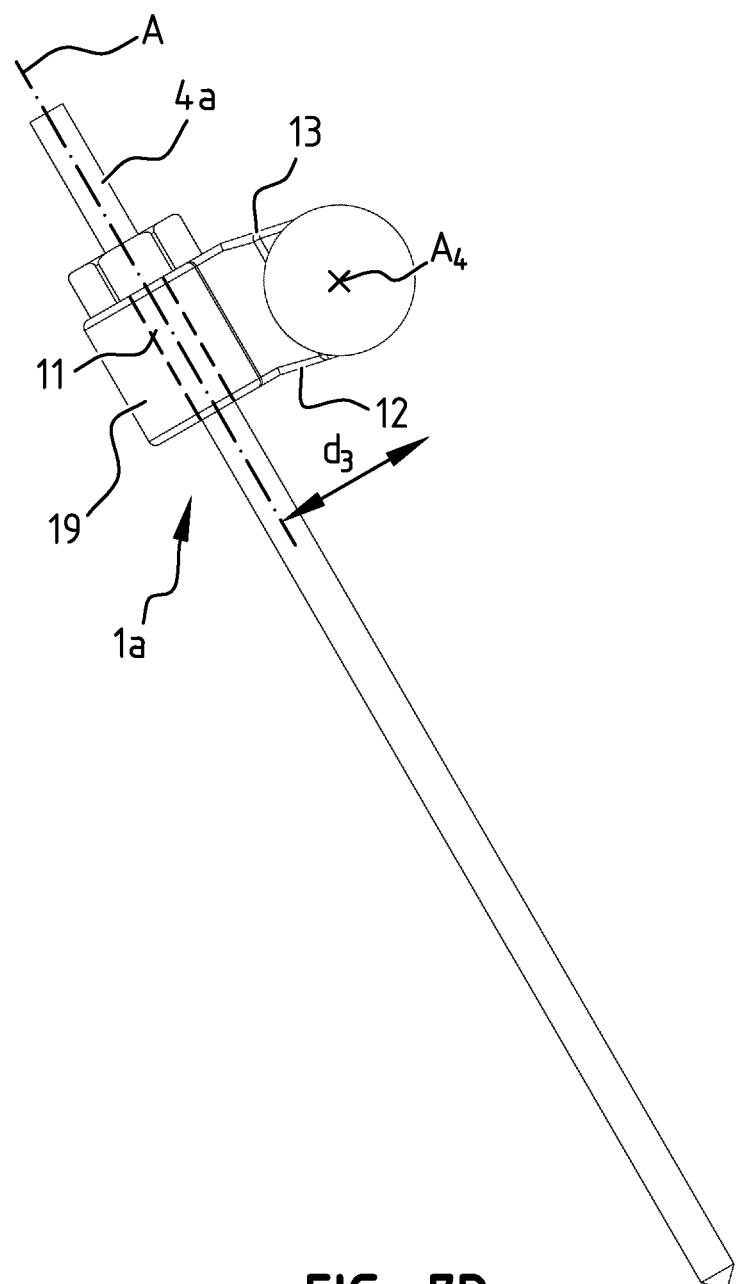
Figure 8:
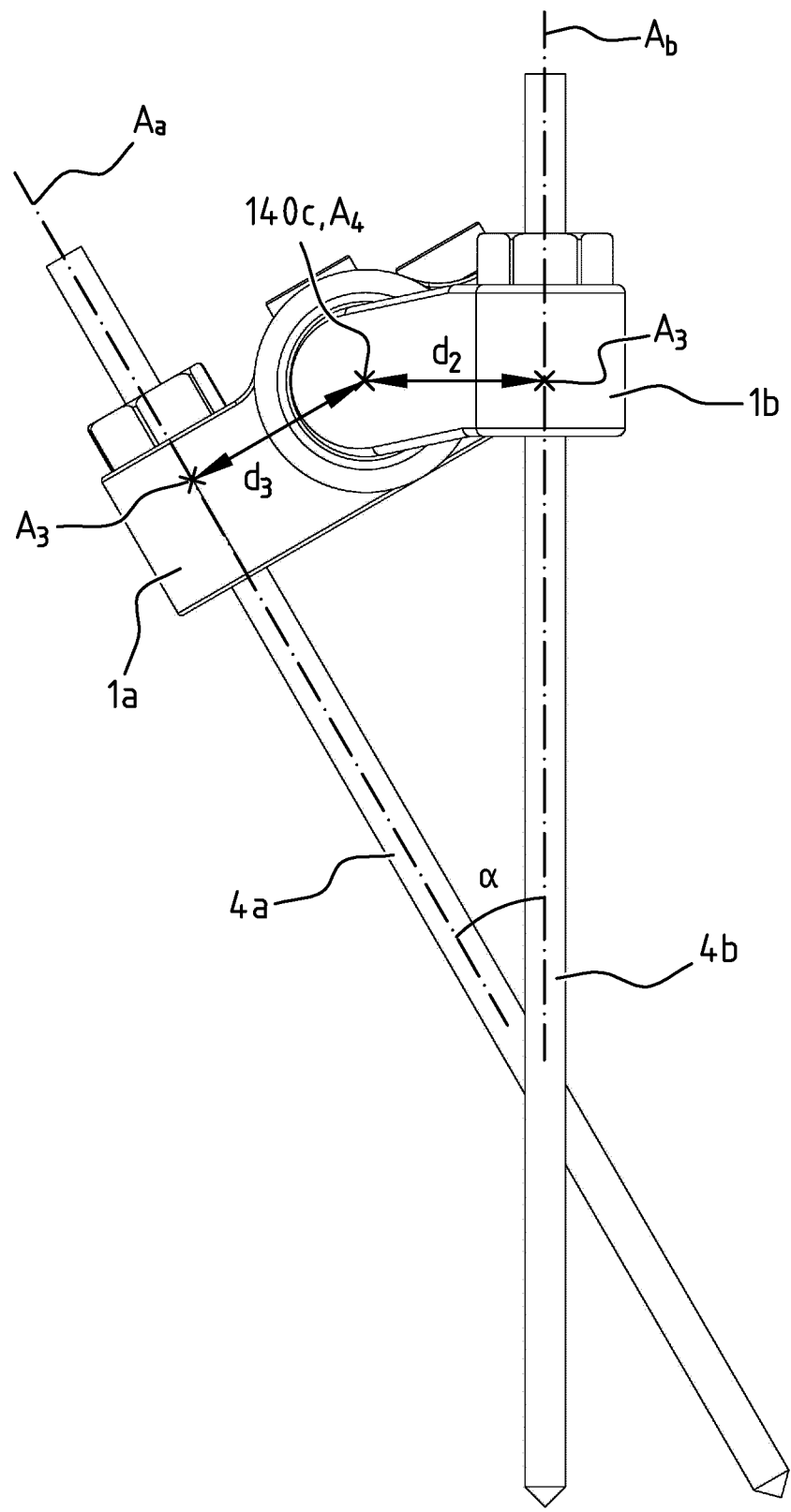

FIGS. 6a-c shows a first connection device of the distractor of FIG. 5 in perspective, top view and side view respectively;

FIGS. 7a-d shows a second connection device with distraction mechanism in perspective, top view in two positions and in side view respectively;

FIG. 8 shows the positional relationship of the bone pins of the two connection devices in side view;

FIGS. 9 and 10 show a joint knee and the femur and tibia in cross section indicating the bone pin positions; and FIGS. 11a-c show a bilateral distraction system according to the invention.

In FIGS. 1a-d the steps for connecting a connection device 1 in the form of a connection block to a bone 100 is shown. The connection block 1 is thereto provided with an opening 11 which extends between a first surface 12, which faces the patient 101, and a second surface 13 which faces away from the patient 101. The opening 11 has a section 11a towards the second surface 13 which is provided with threading 14. Towards the patient facing surface 12, the opening 11 is provided with a tapering section 11b wherein the diameter of the opening 11 becomes smaller in the direction of the patient 101, seen along a longitudinal axis A of the opening 11.

Inserted into the opening is a locking device 2 which has a substantially annular shape and is shaped to fit inside the opening 11. The locking device 2 has a flange 21 at one side and deformable tongues 22 at the other side and a body 23 provided there between. The body 23 is provided with threading 24 for cooperation with the threading 14 of the opening. The outer diameter of the body 23 of the locking device 2 thereby corresponds to the diameter of the first section 11a of the opening 11. The length of the body 23 provided with the threading 24 preferably corresponds to the length of the first second 11a of the opening 11, seen along the longitudinal axis A.

Figure 1A:
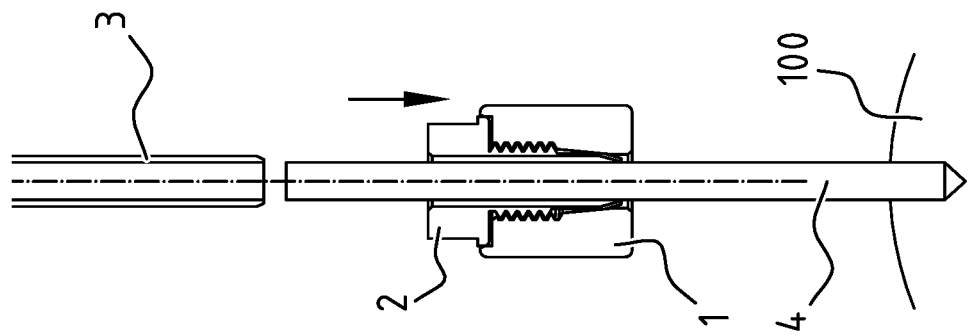

The threading 14, 24 fixes the relative position of the locking device 2 and the connection device 1, which position can be adjusted by rotating the locking device 2. In the position as show in FIG. 1a, the lower surface of the flange 21 extends at a distance from the surface 13, such that further movement of the locking device 2 in a direction indicated with I in FIG. 1a is possible, as will be explained in greater detail below. In the situation as shown in FIG. 1a, the tongues 22 of the locking device 2 only partially extend in the tapering section 11b of the opening 11.

Figure 1B:
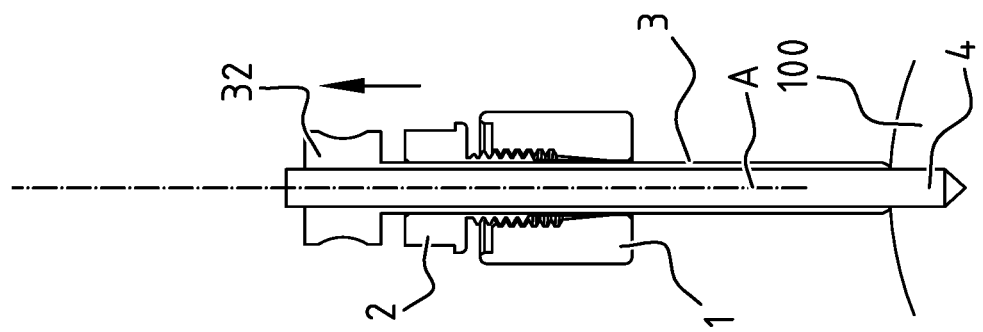

The inner diameter of the locking device 2, including the diameter at the location of the tongues 22, corresponds to the outer diameter d1 of a guiding cannula 3. This limits relative movement of the locking device 2, which also serves as a guiding device for guiding the cannula 3, in a direction along the longitudinal axis A. The guiding cannula 3 is arranged to guide a bone pin 4 from the connection device 1 to the bone 100, see FIG. 1b. In inserted situation as shown in FIG. 1b, the cannula 3 is thereto slidable along the longitudinal axis A with respect to the locking device 2 and thereby with respect to the connection device 2. A flange 32 is provided to allow efficient adjustment of the depth of the cannula 3. This allows efficiently guiding a bone pin 4 to the bone 100, irrespective of the distance between the connection device 1 and the bone 100. When the cannula 3 is advanced sufficiently far such that a distal end 31 abuts the bone 100, the bone screw 4 can be inserted into the cannula 3, schematically indicated with the arrow in FIG. 1b. The inner diameter of the cannula 3 thereto corresponds to the outer diameter of the bone pin 4 such that relative movement of the bone pin 4 in the cannula 3 is again restricted to movement along the longitudinal axis A. The movement of the bone pin 4 with respect to the connection device 1 is therefore also fixed.

Figure 1C:
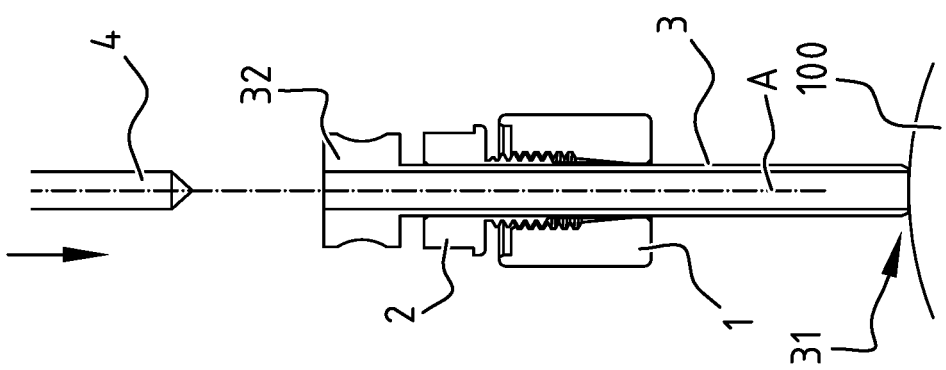

In a next step, see FIG. 1c, the bone pin 4 can be fixed to the bone 100. In this example, self-tapping bone screws 4 are used, such that the bone pins 4 are inserted into the bone 100 by rotating the bone pin 4 inside the cannula 3. The cannula 3 thereby prevents damage to the surrounding tissue of the patient 3. Other bone pins 4 can however be used.

Figure 1D:
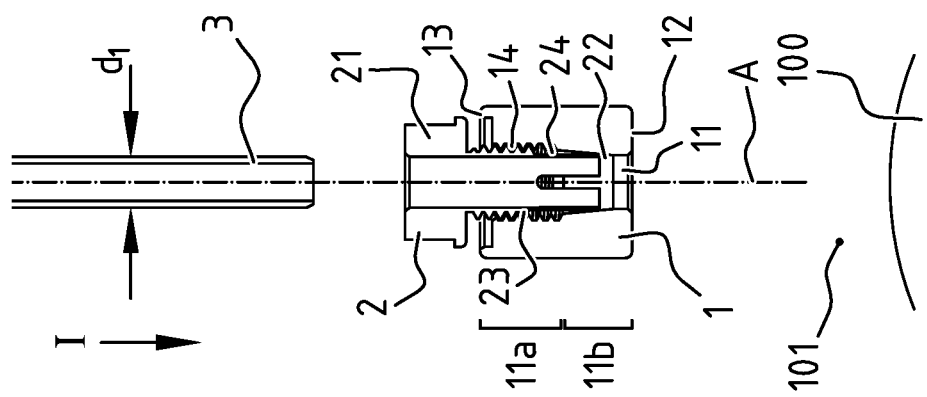

After fixation of the bone pin 4 to the bone 100, the cannula 3 can be withdrawn from the combination of the bone pin 4, the locking device 2 and the connection device 1. This movement is indicated with the arrow in FIG. 1c. As the inner diameter of the locking device 2 corresponds to the outer diameter of the cannula 3, which is larger than the outer diameter of the bone pin 4, the bone pin 4 is held in the locking device 2 with play. Therefore, in order to lock the bone pin 4 with respect to the locking device 2 and thereby with respect to the connection device 1, the locking device 2 is rotated, thereby moving the locking device 2 along the longitudinal axis A, see arrow in FIG. 1d, in the opening 11. The outer surfaces of the tongues 22 will thereby engage the inner surface of the tapering section 11b, urging the tongues 22 radially inwardly, i.e. towards to the longitudinal axis and thereby towards the bone pin 4. The inner surface of the deformable tongues 22 thereby act as engaging surfaces which are arranged to engage the bone pin 4, thereby locking the bone pin 4 with respect the locking device 2 and thereby the connection device 1. In the locked position as shown in FIG. 1d, the lower surface of the flange 21 of the locking device 2 abuts the upper surface 13 of the connection device 1, which is in this example provided with a correspondingly shaped recess to receive the flange 21 in a countersunk manner.

In this situation, the bone pin 4 is firmly locked with respect to the connection device 1. It will be appreciated, as will be explained in greater detail below, that the bone pin 4 can simply be unlocked by rotating the locking device 2, thereby loosening the tongues 22 such that the locking device 2 is again movable with respect to the bone pin 4.

In the example shown in FIGS. 1a-d, the locking device 2 serves to lock the bone pin 4 and to guide the cannula 3. It is however also possible to use a separate guiding device to guide the cannula 3. Moreover, in the above example, the relative position of the locking device 2 and the connection device 1 is fixed using threading 14, 24. Other means can however be used as will also be shown with reference to FIGS. 2*a-d*

The connection device 1 as shown in FIGS. 2*a-d* is similar to the connection device 1 as shown in FIGS. 1*a-d* and is again provided with an opening 11. The diameter of this opening 11 is again larger than the outer diameter d1 of the cannula 3, such that a guiding device 5 is used to limit the relative movement between the cannula 3 and the connection device 1 along the longitudinal axis A, see FIG. 2*b*. The guiding device 5 again has a annular shape and has an inner diameter corresponding to the outer diameter d1 of the cannula 3. This allows efficient adjustment of the depth of the cannula 3 with respect to the connection device 1 as indicated with double arrow in FIG. 1*b*. Note that this is different from the locking device 2 as used in FIGS. 1*a-d*.

Instead of threading, the guiding device 5 is provided with a deformable part 51 which locks into the opening 11 upon inserting the part 51. The deformable part 51 thereby exerts a clamping action of the inner surface of the opening 11, thereby retaining the guiding device 5 in the opening 11 by friction. The guiding device 5 is further provided with a flange 52 for easy manipulation of the guiding device 5.

Figure 2D:
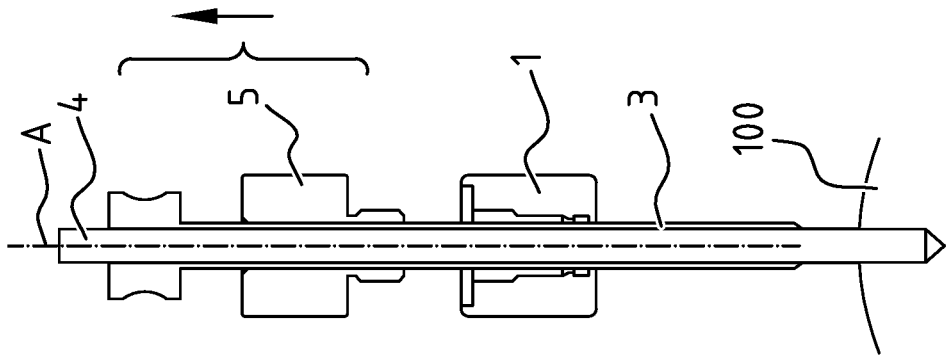
Figure 2C:
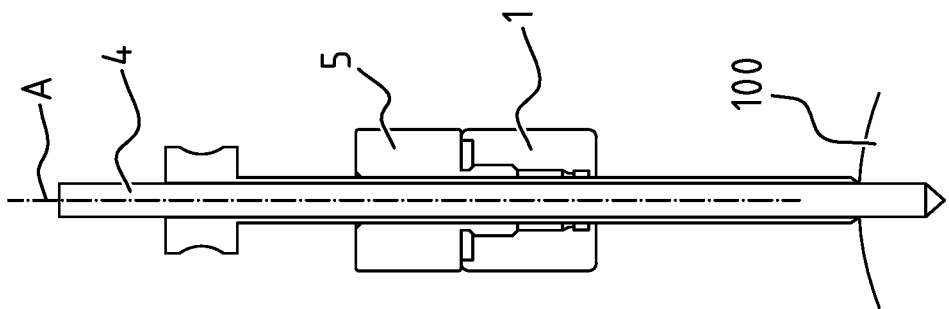
Figure 2B:
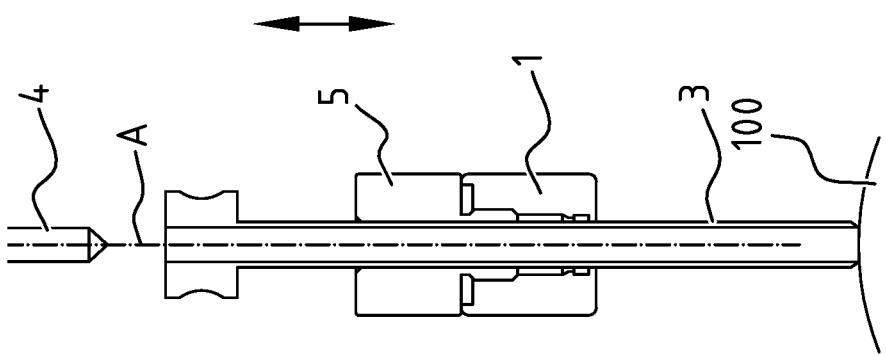
Figure 2A:
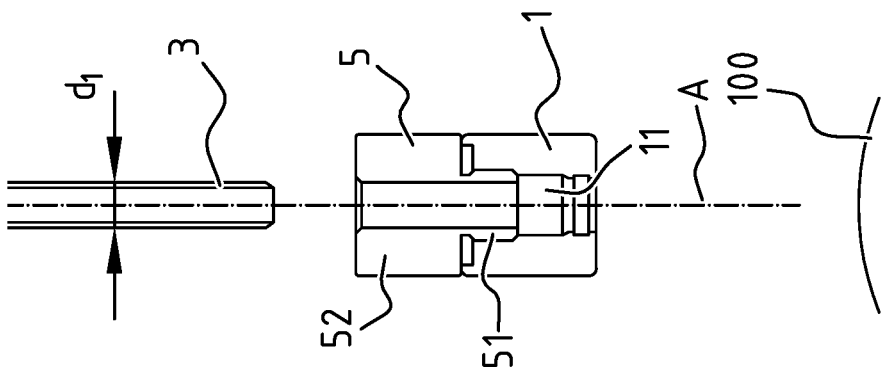

After insertion of the bone pin 4, see FIG. 2*c*, the combination of the guiding device 5 and the cannula 3 can be removed from the combination of the bone pin 4 and the connection device 1, see arrow FIG. 2*d*. As the bone pin 4 is firmly attached to the bone, the combination can be withdrawn by pulling sufficiently hard to overcome the friction of the deformable part 51 of the guiding device 5. The cannula 3 and the guiding device 5 can hereby be removed in unison.

Figure 3A:
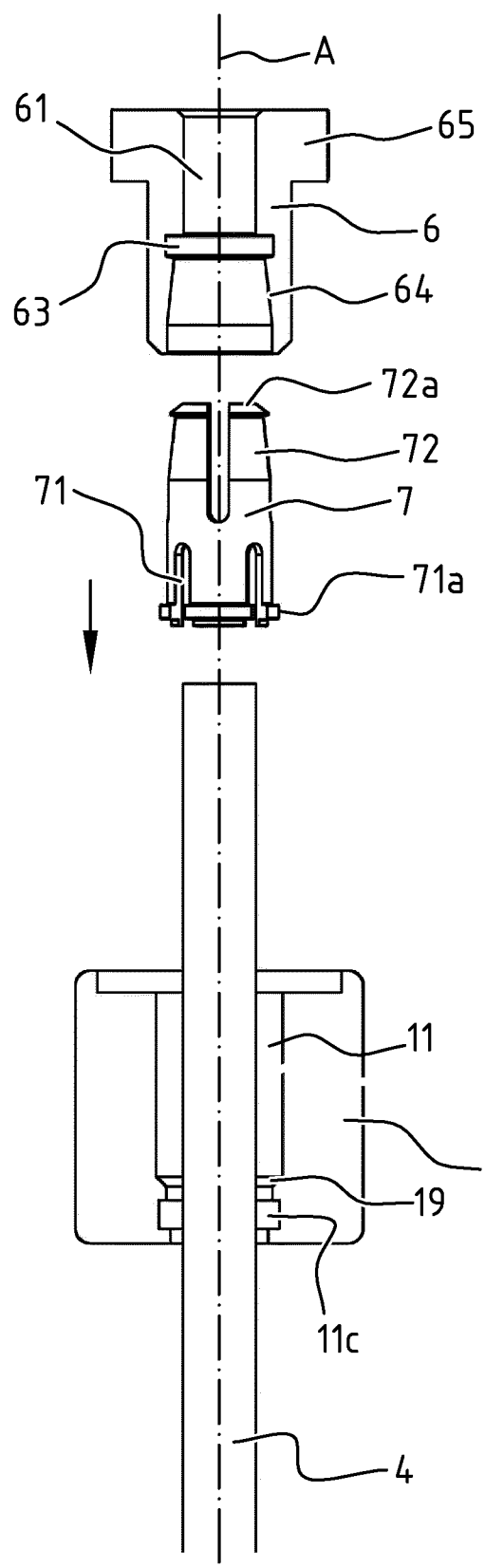
Figure 3B:
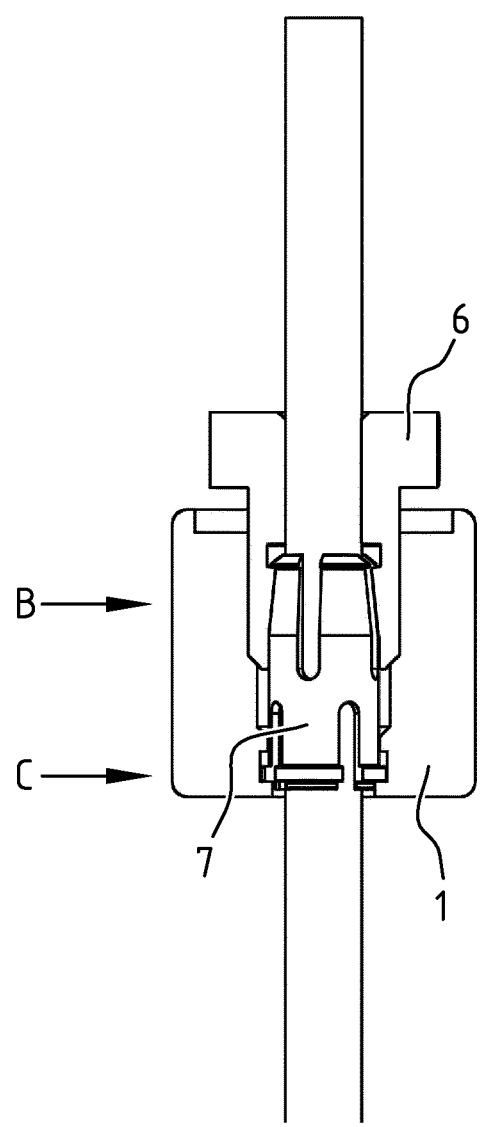

Although a locking device similar to the locking device as shown in FIGS. 1*a-d* can be used to lock the bone pin 4 with respect to the connection device 1, for instance by providing corresponding threading, it is also possible to use a locking mechanism formed of two separate parts, as is shown in FIGS. 3*a* and 3*b*.

The locking mechanism comprises a driving element 6 and a locking element 7, wherein the annularly shaped locking element 7 is provided with sets of tongues 71, 72 at either side. Both sets of tongues 71, 72 are arranged to move radially inwardly upon deformation, thereby locking the bone pin 4. The first set of tongues 71 at the lower side of the locking element 7 are moved radially inwardly upon moving, or driving, the locking element 7 in a direction indicated with the arrow in FIG. 1*a*. The reduction of the diameter indicated with 19 in the opening 11 will thereby urge the tongues 71 towards the outer surface of the bone pin 4. A groove 11*c* is provided near end of the opening 11 towards the patient, wherein ribs 71*a* of the tongues 71 can snap for locking the relative positions of the locking element 7 with respect to the connection device 1. In this locked position, the tongues 71 exert a firm clamping action on the bone pin 4 at a location along the longitudinal axis A indicated with the arrow C in FIG. 3*b*, thereby preventing movement of the bone pin 4.

To further improve the locking action, also to the tongues 72 provided on the upper side of the locking element 7 will be urged radially inwardly upon movement of the driving element 6 towards the locking element 7. More specifically, the annularly shaped driving element 6 is provided with an opening 61 of which the lower section 64 has a tapering diameter, wherein the diameter increases towards the lower side. The tapering section 64 forms a guiding surface for urging the tongues 72 inwardly, i.e. towards the bone pin 4, when the driving element 6 is moved towards the locking element 7.

Also the tongues 72 can be provided with ribs 72*a* which can be received in a correspondingly shaped groove 63 at the end of the guiding surface. This connects the driving element 6 to the locking element 7 and thereby to the connecting device 1. In the situation as show in FIG. 3*b*, the tongues 72 exert a clamping action on the bone pin 4 at a location along the longitudinal axis A indicated with B, at a distance from location C. This improves the locking action of the locking mechanism.

The locking system may but not necessarily make use of ribs (71*a*/11*c* and 72*a*/63) and corresponding grooves at either side or at both sides, to fix the 7 into the connecting device 1 or the driving element 6 or both.

The connection system as described above is particularly suitable to connect a connection device to a bone with two parallel bone pins. This is explained with reference to FIG. 4. Although in this figure a connection system is shown which corresponds to the system as shown in FIGS. 1*a-d*, it will be appreciated that the same applies to the system as shown in FIGS. 2 and 3, or combinations thereof.

Figure 4:
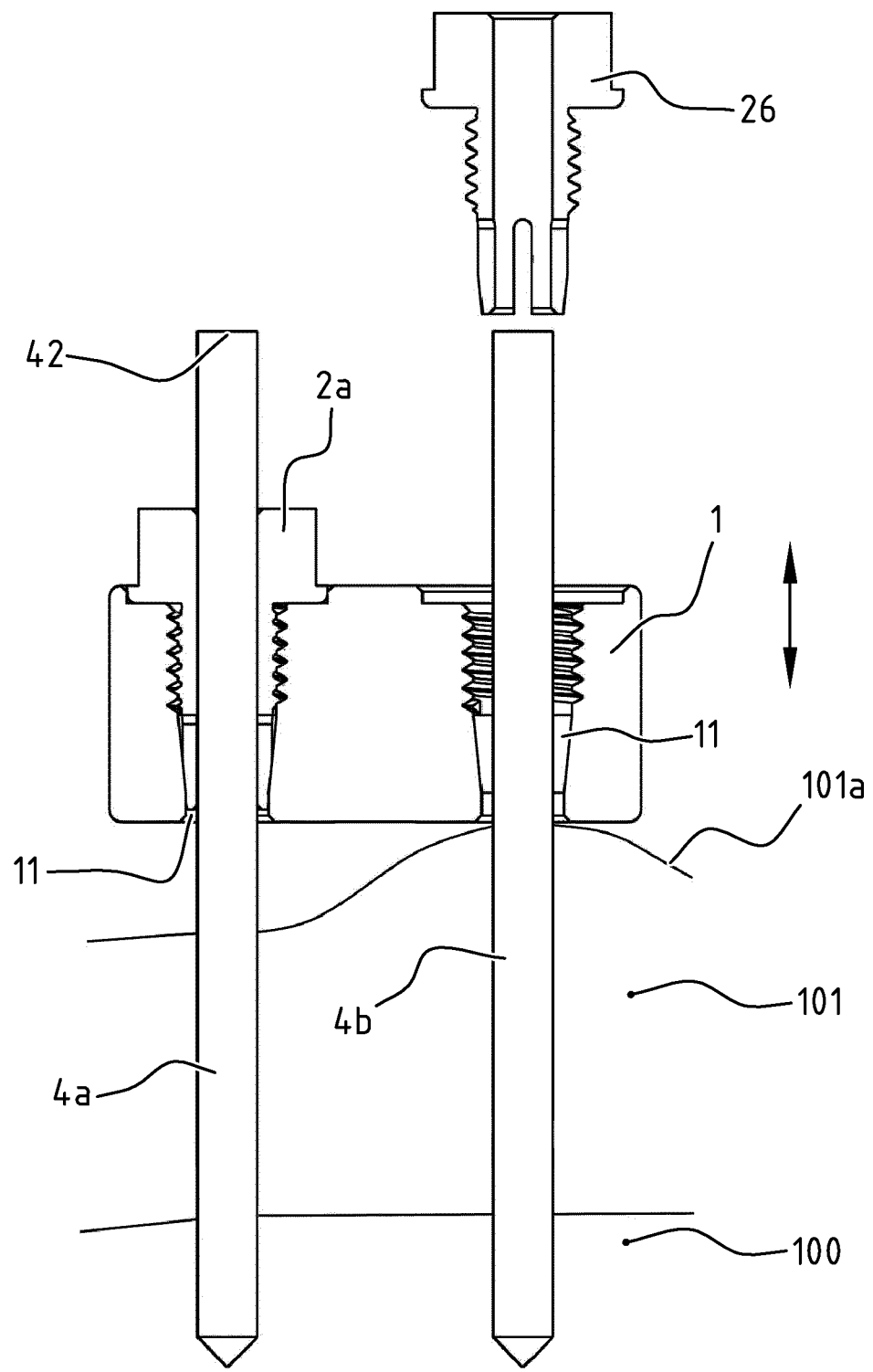
FIG. 4 shows a variant of a connection device having two openings.

In FIG. 4, a connection device 1 is shown provided with two parallel openings 11, into which bone pins 4*a* and 4*b* are inserted. In this example, bone pin 4*a* was inserted first by using a separate cannula to drill the bone pin 4*a* into the bone 100. After fixation of this bone pin 4*a*, the connection device 1 was advanced over the proximal end 42 of the pin 4*a* and the pin 4*a* was locked with respect to the connection device 1 using a locking device 2*a*. In order to ensure that a second pin 4*b* was inserted parallel to the first bone pin 4*a*, the connection method similar to the methods shown in FIGS. 1 and 2 was used to insert and connect the bone pin 4*b*. A cannula is thereby used to guide the bone pin 4*b* to the bone 100, the surface of which differs in terms of height from the surface of the first bone pin 4*a* as shown in FIG. 4.

In this example however, a separate guiding device was used (similar to the method of FIG. 2) to guide the cannula, although a locking device in one piece was used (similar to the locking device of FIG. 1). Moreover, the interconnection of the locking devices 2*a* and 2*b* (and the guiding devices which are not shown) with the connection device 1 is obtained with corresponding threading, again similar to the embodiment of FIG. 1. The situation of the bone pin 4*b* as shown in FIG. 4 thus corresponds to the situation of FIGS. 2*d* and 3*a*: after guidance and insertion of the pin and prior to locking of the pin 4*b*.

Using a connection device 1 having two parallel openings for receiving bone pins, ensures that after fixation of a first bone pin in the bone, a second bone pin will be inserted into the bone parallel to the first bone pin. The guiding device and the cannula after all limit movement of the bone pin with respect to the connection device along the longitudinal axis of the opening. The connecting element as such guiding the second bone pin to a preferred anatomical position.

Providing parallel bone pins allows adjusting the distance between the connection device 1 and the patient 101, of which the skin 101*a* is schematically indicated in FIG. 4. In case of for instance a swelling, as schematically indicated around bone pin 4*b*, the locking devices 2*a* and 2*b* may be loosened, in this example by rotating the locking devices 2*a*, 2*b*, such that the connection device 1 is again movable with respect to the bone pins 4*a*, 4*b*, schematically indicated with the double arrow in FIG. 4. After displacement of the connection device 1 along the longitudinal axes of the bone pins, the locking devices 2a, 2b can again be tightened to lock the bone pins 4a, 4b with respect to the connection device 1.

In the following figures, an external orthopaedic device, in this example in the form of a distractor 110 is explained. The external distractor 110 of this example is arranged to distract, that is gradually enlarge, the joint space width of the knee joint. The distractor 110 is thereto provided with connection devices 1a, 1b to receive and lock the pins 4a, 4b with locking devices 2. Connection device 1a is arranged to be connected to the tibia with two parallel bone pins 4a, whereas connection device 1b is arranged to be connected to the femur using two parallel bone pins 4b. It is noted that although it is preferred to use a connection system as shown in any of the FIGS. 1-4 to connect the bone pins 4a, 4b to the respective bones, this is not strictly necessary. Other suitable connection systems may be used.

The connection devices 1a, 1b are interconnected by an interconnecting system 120. The interconnection system 120 comprises a central tubular member 123 of which both ends comprise receptacles 121a,b arranged to receive balls 140a, b (see for instance FIGS. 6a and 7a) of the connection devices 1a, b for forming ball joints. The receptacles 121a, b for the balls 140a,b are arranged to receive the balls 140a, b in a rotating manner in an unlocked position and to prevent any relative movement of the balls 140a, b with respect to their respective receptacles 121a,b in a locked position. In the unlocked position, the connection devices 1a, 1b are substantially free to rotate and angulate with respect to the central tubular member 123, while in the locked position, the relative positions of the connections devices 1a, 1b are fixed with screw 122.

With reference to FIGS. 6a-c, the connection device 1b is provided with two openings 11 which extend between a patient facing surface 12 and an outer surface 13. Both openings 11 are oriented parallel with respect to each other. The longitudinal axes A of the openings, and thus of the inserted bone pins 4b, therefore also extend parallel. As mentioned above, the connection device 1b is provided with a ball 140b to form a ball joint when inserted into the receptacle of the interconnecting system 120. With specific reference to FIG. 6b, it can be seen that the ball 140b, in particular the centre 140c thereof, extends at a distance d2 from an axis A3 extending though (the centres of) both openings 11. The axis A3 is perpendicular to the longitudinal axes A of the openings. The distance d2 is in this example determined as the minimal distance between the axis A3 and the pivot point 140c. As shown in FIG. 6c, this construction creates an offset d2 of the longitudinal axes A of the openings 11 (and thereby of the bone pins 4b) with respect to the pivot point 140c. FIG. 6c further illustrates that the lower surface 12 of the connection device 1b is curved (bended) towards the patient, seen in the direction from the pivot point 140c towards the openings 11 in the lower surface 12, enabling optimal intuitive guidance to anatomically preferred positions of the bone pins with proper mechanical characteristics of the whole configuration of device and bones.

The other connection device 1a is discussed in greater detail with reference to FIGS. 7a-d. Also this connection device 1a is provided with two parallel openings 11 for receiving two parallel bone pins 4a. The openings 11 again extend between a patient facing surface 12 and an outer surface 13. Also this connection device 1a is provided with a ball 140a to form a ball joint in combination with the receptacle 121a of the connecting system 120.

The connection device 1a is however further provided with a distraction mechanism, generally indicated with 130. The distraction mechanism comprises means to adjust the distance between the bone pins 4a and 4b of the two connection devices 1a, 1b. More specifically, the distraction mechanism is arranged to gradually increase the distance between the pivot point 140c of the ball 140a and the openings 11 for the bone pins 4a. This is achieved by cooperating threading provided on the support 131 of the ball 140a and rotatable ring 132 at the end of a tubular base body 134 of the connection device 1a. Rotation of the ring 132 will adjust the distance L1 between the base body 134 and the ball 140a, as is visible in FIGS. 7b and 7c. This allows adjusting the length L1 along an adjustment axis A4. In this example, the adjustment axis A4 is defined to extend through the centre 140c of the ball 140a forming the pivot point of the ball joint.

It will be appreciated that the adjustment of the length L1 along the adjustment axis A4 can take place without loosening the tension or structural integrity between the two connection devices 1a, 1b, thereby keeping the joint at the preferred relative distance. In order to allow adjustment of the distance between the two sets of bone pins 4a, 4b prior to use, the connection device 1a comprises a body 19 which is arranged slidable along the tubular body 134 in a direction L2. Movement of the body 19, which is provided with the openings 11, can be locked using the screw 19a.

In order to still allow little displacement along the adjustment axis A4 during use of the patient, the stem 133 of the ball 140a is resiliently supported, in this example using a spring, in the support 131 of the ball 140a. Support 131 and stem 133 are thus allowed to move, as indicated with the double arrow L3 along the adjustment axis A4.

Although the ball 140a is allowed to move with respect to the openings 11 for receiving the bone pins 4a, due to the distraction mechanism 130 or the sliding movement between the body 19 and the tubular body 134, the relative orientation of the openings 11 along an axis A3 with the respect to the adjustment axis A4 remains unchanged. The axis A3 extending between the two centres of the openings 11 and perpendicular to the longitudinal axes A thereof extends at a distance d3 and parallel to the adjustment axis A4. The same offset d3 is also visible in FIG. 7d, wherein also a curved patient facing surface 12 is shown as option.

As is already clear from FIG. 5, the offset of the bone pins 4b in the connection device 1b is opposite to the direction of the offset in the connection device 1a with the distraction mechanism 130. This relative orientation is further shown in FIG. 8, which is a view of the system of FIG. 1 along arrow VIII in FIG. 5.

In FIG. 8 it can be seen that the longitudinal axes Aa, Ab of the two sets of pins 4a, 4b extend under an angle α with respect to each other. The offset d2, i.e. the distance between the adjustment axis A4 (also the pivot point 140c) and the axis A3 through the openings 11 of the connection device 1b is in the opposite direction of the offset d3, i.e. the distance between the axis A3 through the openings 11 in the connection device 1a and the pivot point 140c. It also shows the curvature in this case in one of the connecting devices 1b. This configuration allows an efficient placement of the distractor 110 on the patient, with preferred anatomical location of bone pins, preventing damage to or interference with critical tissues.

In case of the knee joint, placement of a distractor 110 on a patient 101 is explained while referring to FIGS. 9 and 10. In a first step of fixing the distractor 110 to the patient 101 to distract the knee joint 101b, a first bone pin 4b is inserted into the femur 101c with an orientation which is posterior (indicated with P in the cross section of FIG. 9b seen along the transverse plane Tp1 of FIG. 9a) with respect to the coronal plane Cp. This prevents damage to and/or interference with sensible tissue. For the fixation of the first pin 4b, a separate cannula may be used to connect the bone pin 4b to the bone 101c. After fixation of the first bone pin 4b, a connection device 1b of the distractor 110 is connected to the bone pin 4b. The connection device 1b is then aligned such that the axis A3 between the openings 11 is aligned to be substantially parallel to the longitudinal axis Af of the femur 101c. The connection device 1b is then used as drill guide, preferably using the system as shown in FIGS. 1-4, to insert a second bone pin 4b parallel to the first bone pin 4b at the location of the transverse plane Tp2. Bone pins 4b then extend parallel and perpendicular to the longitudinal axis Af of the femur 101c.

As the interconnecting system 120 of the distractor 110 is in the unlocked position, the connection device 1a provided with the distraction mechanism 130 is freely movable with respect to the already fixed connection device 1b. As it is important that the adjustment axis A4 of the distraction mechanism 130 is parallel to the longitudinal axis At of the tibia 101d, (FIG. 10) the connection device 1a is arranged such that the adjustment axis A4 is parallel to said longitudinal axis At of the tibia 101d. This can be done by aligning the axis A3 through the openings 11 in the connection device 1a to be parallel to the longitudinal axis At of the tibia 101d.

Figures 10A, 10B:
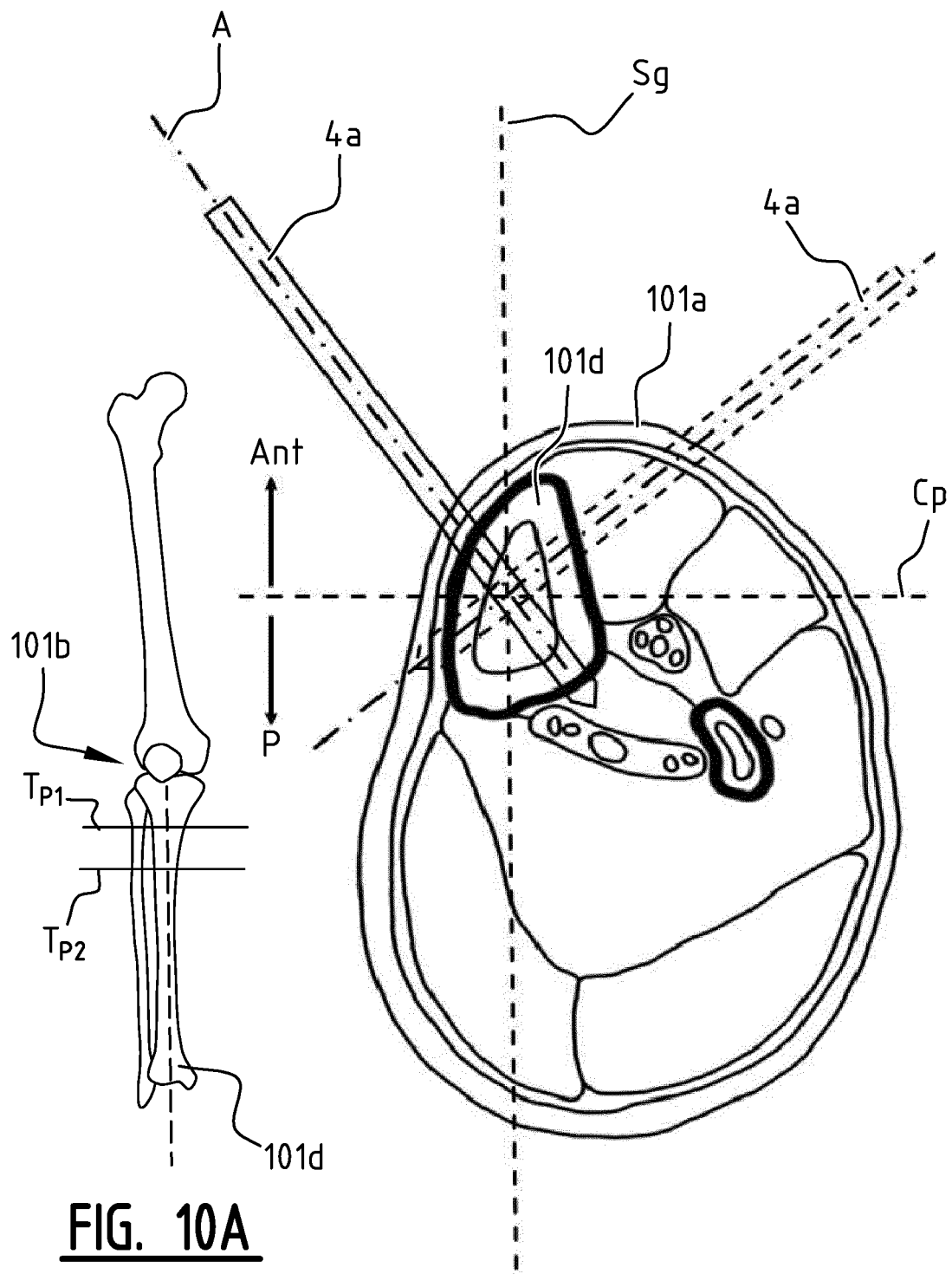

With reference to FIGS. 10a and 10b, the trajectories A of the bone pins 4a are chosen to be anterior (indicated with Ant in the transverse section of FIG. 10b along plane Tp1 in FIG. 10a) with respect to the coronal plane Cp. This prevents damage to and/or disturbance of sensible tissue. It is hereby noted that the configuration of the distractor 110 and more in particular the offsets d2 and d3 as shown in FIG. 8 automatically forces the posterior placement of the bone pins 4b in the femur 101c and the anterior placement of the bone pins 4a in the tibia 101 (intuitive guiding of optimal anatomical positions of bone pins by the device). The bone pins 4a are inserted into the bone 101d using the openings 11 of the connection device 1a as drill guides, preferably using the method as shown in FIGS. 1-4.

After correct fixation of the two connection devices 1a and 1b at preferred distance from the bone/skin enabled by parallel pins), the interconnection system 120 can be moved to the locked position, thereby fixing the relative positions of the connection devices 1a, 1b.

It is possible to use the distractor 110 as an unilateral distractor. It is however also possible to use the distractor in a bilateral configuration. For that case, a second distractor having a configuration which is mirror symmetrical with respect to the sagittal plane Sg (see FIGS. 9B and 10b) is connected to the patient. The orientation of the bone pins 4a, 4b for the femur 101c and tibia 101d is indicated in phantom in FIGS. 9b and 10b. This configuration is shown in FIGS. 11a-c, wherein FIG. 11a shows a transverse section in the femur 101c, FIG. 11b shows a transverse section in the tibia 101d and FIG. 11 is a side view of the system.

The present invention is not limited to the embodiment shown, but extends also to other embodiments falling within the scope of the appended claims.

The invention claimed is:

1. A system for connecting a connection device to a bone with a bone pin, wherein the connection device is provided with an opening for receiving the bone pin, wherein the system comprises:
   said connection device;
   a guiding tube arranged to guide the bone pin from the connection device to the bone for connecting the bone pin to the bone, wherein the inner diameter of the guiding tube corresponds to the outer diameter of the bone pin and wherein the guiding tube can be slidably received in the opening, the guiding tube being slidable with respect to the connection device along only an axis colinear to a longitudinal axis of the opening; and
   a locking device arranged to be received in the opening of the connection device and arranged to engage the bone pin for locking the bone pin with respect to the connection device,
   wherein the system is arranged to guide the guiding tube and to prevent any movement of the guiding tube relative to the opening of the connection device other than a sliding movement along the longitudinal axis, and
   wherein the guiding tube is movable with respect to the connection device and bone pin such that the guiding tube is removable from the combination of the bone pin and the connection device and wherein the locking device is arranged to lock the bone pin after removal of the guiding tube.

2. The system according to claim 1, wherein the locking device has an annular body having an outer diameter corresponding to the diameter of the opening of the connection device and an inner diameter suitable for engaging the bone pin.

3. The system according to claim 1, wherein the locking device comprises an engaging surface for engaging the bone pin, wherein the engaging surface is movable towards and from said bone pin between an unlocked position, wherein the bone pin is movable with respect to the engaging surface, and a locking position, wherein the engaging surface engages the bone pin for locking said bone pin with respect to the connection device by clamping.

4. The system according to claim 3, wherein the locking device has an inner diameter substantially corresponding to the diameter of the bone pin.

5. The system according to claim 3, wherein the locking device has an inner diameter substantially corresponding to the outer diameter of the guiding tube in the unlocked position.

6. The system according to claim 3, wherein the opening of the connection device has a tapering diameter, seen along the longitudinal axis of the opening, for moving the engaging surface between the positions upon longitudinal movement of the locking device with respect to the connection device.

7. The system according to claim 6, wherein the locking device comprises a correspondingly shaped tapering outer diameter.

8. The system according to claim 3, wherein the locking device comprises a deformable element arranged to deform in the locked position for engaging the bone pin.

9. The system according to claim 8, wherein the opening is provided with a recess, preferably a groove, for receiving the deformable element for locking the connection device and the locking device.

10. The system according to claim 3, wherein the locking device comprises an engaging element provided with at least one engaging surface and a separate driving element arranged to move the engaging element along the longitudinal axis of the opening for moving the engaging surface from the unlocked to the locked position.

11. The system according to claim 10, wherein the engaging element comprises at least one second engaging surface at a distance from the first engaging surface, seen along the longitudinal axis of the opening, wherein the driving element is provided with an opening for receiving the engaging element and wherein the opening of the driving element has a tapering diameter, seen along the longitudinal axis of the opening, for moving the second engaging surface between the an unlocked and locked position upon longitudinal movement of the driving element with respect to the engaging element.

12. The system according to claim 10, wherein the driving element and the opening of the connection device are provided with cooperating connecting means.

13. The system according to claim 1, wherein the opening comprises, seen along the longitudinal axis of the opening, a first section having a first diameter and a second section having a second diameter corresponding to the outer diameter of the guiding tube, wherein the first diameter is larger than the second diameter.

14. The system according to claim 13, wherein the opening comprises a tapering section extending between the first and the second sections in which the diameter tapers from the first diameter towards the second diameter.

15. The system according to claim 13, wherein the connecting means are provided in the first section of the opening.

16. The system according to claim 13, wherein the guiding element has an annular body having an outer diameter corresponding to the diameter of the first section of the opening.

17. The system according to claim 1, wherein the opening of the connection device and the locking device are provided with cooperating connecting means for interconnecting the locking device and the connection device.

18. The system according to claim 17, wherein the opening and the locking device are provided with cooperating threading.

19. The system according to claim 17, wherein the guiding element is provided with corresponding connecting means for interconnecting the guiding element and the connection device.

20. The system according to claim 1, further comprising a guiding element for guiding the guiding tube and for preventing any movement of the guiding tube relative to the opening of the connection device other than a sliding movement along the longitudinal axis, wherein the guiding element is arranged to be received in the opening of the connection device, wherein the guiding element has an outer diameter corresponding to the diameter of the opening and wherein the guiding element has an inner diameter corresponding to the outer diameter of the guiding tube, wherein the guiding element and the guiding tube are removable from the combination of the bone pin and the connection device.

21. The system according to claim 20, wherein the driving element is formed as the guiding element.

22. The system according to claim 1, further comprising a second locking device, wherein the connection device comprises a second opening for receiving a second bone pin, wherein the longitudinal axes of the first and the second openings are substantially parallel and wherein the second locking device is arranged to lock the second bone pin after removal of a guiding tube from the second opening.

23. An external orthopaedic device arranged to be connected between a first bone part and a second bone part, wherein the orthopaedic device comprises a first connection device as defined in claim 1 and a second connection device.

24. A method for connecting a connection device to a bone with a system according to claim 1, wherein the method comprises the steps of:
 providing a bone pin in said guiding tube in the opening of the connection device;
 guiding the guiding tube to the bone by sliding said guiding tube in the opening of the connection device with respect to said connection device, such that the guiding tube abuts the bone;
 inserting the bone pin into the bone;
 removing the guiding tube from the combination of the bone pin and the connection device after insertion of the bone pin; and
 locking the bone pin with respect to the connection device with said locking device after removal of the guiding tube.

25. The system according to claim 1, wherein the connection device is arranged to guide the guiding tube and to prevent any movement of the guiding tube relative to the opening of the connection device other than a sliding movement along the longitudinal axis.

26. The system according to claim 1, wherein the locking device is arranged to guide the guiding tube and to prevent any movement of the guiding tube relative to the opening of the connection device other than a sliding movement along the longitudinal axis.

* * * * *